United States Patent [19]

Smith

[11] Patent Number: 5,567,624
[45] Date of Patent: Oct. 22, 1996

[54] CARBAZINE DYES AND DERIVATIVES FOR PH MEASUREMENT

[75] Inventor: Roger E. Smith, Bountiful, Utah

[73] Assignee: Utah Medical Products, Inc., Midvale, Utah

[21] Appl. No.: 429,622

[22] Filed: Apr. 27, 1995

[51] Int. Cl.$^6$ .......................... G01N 31/22; G01N 21/64; C07D 219/00

[52] U.S. Cl. .......................... 436/163; 8/662; 422/82.05; 422/82.06; 422/82.07; 422/82.08; 436/164; 436/166; 436/172; 546/15; 546/16; 546/17; 546/18

[58] Field of Search .............................. 422/82.05–82.08; 436/163–164, 166, 169, 172; 546/15–18; 8/662

[56] References Cited

U.S. PATENT DOCUMENTS

| | | |
|---|---|---|
| 3,781,711 | 12/1973 | Drexhage et al. |
| 3,801,579 | 4/1974 | Schmidt et al. .......................... 546/18 |
| 4,139,342 | 2/1979 | Sheldrake et al. .......................... 8/4 |
| 4,320,939 | 3/1982 | Mueller .......................... 351/44 |
| 4,716,222 | 12/1987 | Wallenfels et al. .......................... 536/18.7 |
| 4,810,636 | 3/1989 | Corey .......................... 435/14 |
| 4,874,813 | 10/1989 | O'Shannessy .......................... 525/54.1 |
| 4,932,871 | 6/1990 | Bell el al. .......................... 435/97 |
| 4,945,171 | 7/1991 | Haugland et al. .......................... 549/224 |
| 5,104,980 | 4/1992 | Corey .......................... 536/18.1 |
| 5,208,326 | 5/1993 | Corey .......................... 536/53 |
| 5,308,581 | 5/1994 | Lippitsch et al. .......................... 422/82.08 |

OTHER PUBLICATIONS

V. B. Piskov et al. *Chem. Abstr.* 1972, 77, 34112t.
J. E. Adams et al. *J. Am. Chem. Soc.* 1973, 95, 5477–5481.
R. B. Beissner et al. *J. Chromatog.* 1978, 161, 127–135.
H. C. Lee et al. *Biochim. Biophys. Acta* 1980, 601, 152–166.
K. Hiraki et al, *Bunseki Kagaku* 1981, 30, 45–50.
P. D. Verweij et al. *Reu. Trav. Chim. Pays Bas* 1992, 111, 371–378.
A. Rumphorst et al. *J. Fluores*, 1994, 4, 45–48.
The Phenol Dyestuff of Liebermann as an Acridan Derivative by, Robert Hill, G. R. Bedford and B. R. Webster.

*Primary Examiner*—Arlen Sodehquist
*Attorney, Agent, or Firm*—Thorpe, North & Western, L.L.P.

[57] ABSTRACT

A composition for determining pH of a solution comprises a fluorescent carbazine dye covalently bound to a solid support. A method of determining pH of a solution comprises placing the composition in the solution, contacting the composition with a selected wavelength of light to excite fluorescence by the carbazine dye, measuring intensities of the fluorescence at two selected wavelengths, calculating a ratio of fluorescence intensities at the two selected wavelengths, and correlating the ratio with a predetermined relationship of such ratios to pH. A fiber optic system for measuring pH of a solution with the carbazine-dye-containing composition is also disclosed.

83 Claims, 7 Drawing Sheets

CARBAZINE DYES AND DERIVATIVES FOR PH MEASUREMENT

BACKGROUND OF THE INVENTION

This invention relates to carbazine dyes and derivatives thereof for purposes of pH measurement. More particularly, the invention relates to carbazine dyes, compositions containing carbazine dyes bonded to solid supports, and methods of using such carbazine dyes and compositions for measuring pH.

Hydrogen ion concentration or pH is an extremely important parameter in biological and many chemical systems. Many chemical and biological reactions require close regulation of pH for reactions to occur properly. For example, a complex natural process for the control of pH occurs in human blood, which normally has a pH of about 7.4. Variations of even a few tenths of a pH unit can cause serious illness or death. The carbon dioxide concentration of the blood affects the pH significantly because of the propensity of $CO_2$ to combine with water to form carbonic acid. Hemoglobin plays a crucial role in regulation of blood pH by transporting carbon dioxide from the capillaries to the lungs and also by playing a role, with plasma proteins, as a buffer. The lungs ordinarily remove carbon dioxide from the blood as fast as it is formed, thus helping to maintain a constant pH. The kidneys also have a primary role in regulating the hydrogen ion concentration of the intracellular and extracellular fluids by secreting acidic or basic constituents when these deviate from normal and restoring the balance thereof.

Although a variety of techniques have been developed to measure pH, they generally are based on either electrochemical or optical principles. A standard laboratory pH meter, for example, comprises a standard electrode of known potential, a special glass electrode that changes potential depending on the concentration of hydrogen ions in the solution into which it is dipped, and a potentiometer that measures the potential between the two electrodes. The potentiometer reading is automatically converted electronically to a direct reading of the pH of the solution being tested. Indicators, on the other hand, are dyes that change optical properties, such as absorbance or fluorescence, with changes in pH. The greatest sensitivity of indicators to small changes in pH occurs when the equilibrium constant between the acidic and basic forms of the indicator, i.e. the $pK_a$, is near the pH of the medium being measured.

As a broad generalization, optical pH measurement is considered inferior to electrochemical techniques, primarily because factors other than hydrogen ion concentration, such as temperature, ionic strength, and protein concentration, affect the dyes and interfere with pH measurement. Nevertheless, optical techniques have strong advantages where cost and size are concerned. Among the optical techniques, methods based on fluorescence are more sensitive than those based on absorbance due to the well known sensitivity advantage for measuring emitted versus absorbed light. Unfortunately, fluorescence emission from typical dyes is substantially more sensitive to interfering factors than is absorbance. Measurement of pH-dependent emission intensity in single cells or on fiber optics with a single excitation wavelength suffer spurious results related to dye concentration, photobleaching of the dye, and cell thickness or path length.

A solution to the problem of dye concentration is to determine the ratio of the amount of fluorescence at a fixed wavelength with excitation at a pH-sensitive wavelength to the amount of fluorescence at the same wavelength with excitation at a relatively pH-insensitive wavelength. This method is commonly used to estimate the pH inside cells with fluorescein derivatives, e.g., Paradiso et al., 325 Nature 477 (1987), and is practical for suspensions of cells and in homogeneous fluids in a research fluorometer or microscope. It is usually impractical, however, to produce two different wavelengths of light of known intensity for exciting fluorescence in flow systems, including flow cytometers and fiber optic systems, for continuous monitoring of pH of flowing fluids, such as blood. U.S. Pat. No. 4,945,171 describes xanthene dyes having a fused (c) benzo ring that exhibit the advantages of being able to measure two emission maxima with excitation at only one wavelength, selectivity in exciting the acid and base forms independently and measuring their emission at either single or dual wavelengths, and measuring characteristic pH-dependent absorption or fluorescence excitation spectra. Compared to the carbazine dyes that are the subject of this invention, these xanthine dyes exhibit lower fluorescence, less stability, greater temperature sensitivity, and smaller Stokes shift, and are difficult to immobilize on a solid support.

R. Hill et al., *The Phenol Dyestuff of Liehermann as an Acridan Derivative*, J. Chem. Soc. (C) 2462 (1970), describes an acridan derivative, 7-hydroxyspiro [acridine-9, 1'-cyclohexa-2', 5'-diene]-2(9H), 4'-dione, that has been used as an oxidation-reduction indicator. This compound and related acridan derivatives, 4',7-dihydroxyspiro [acridine-9,1'-cyclohexane]-2(9H)-one; 7-hydroxy-2',3',5',6'-tetramethylspiro[acridine-9,1'-cyclohexa-2', 5'-diene]-2(9H), 4'-dione; 9,9-diphenyl-7-hydroxyacridin-2 (9H)-one; and 9,9-dimethyl-7-hydroxyacridin-2(9H)-one, yield blue solutions in sulfuric acid which turn red on dilution, this color being due to protonation of the free base. The neutral forms of the compounds are yellow in most solvents. A method of synthesizing these compounds is also disclosed.

In view of the foregoing, it will be appreciated that pH-sensitive dyes and methods of use for determining pH, with reduced sensitivity to potentially interfering factors and substantially improved pH measurement performance in biological systems, most of which function in the pH range of 5 to 9, would be a significant advancement in the art.

OBJECTS AND SUMMARY OF THE INVENTION

It is an object of the present invention to provide pH-sensitive fluorescent dyes and methods of use thereof for determining pH.

It is another object of the invention to provide fluorescent dyes and a method of optical pH measurement that greatly reduce the inhibitory effects of temperature, ionic strength, and presence of other molecules such as proteins.

It is also an object of the invention to provide fluorescent dyes and a method of optical pH measurement that substantially improve pH measurement in biological systems in the range of pH 5 to 9.

It is still another object of the invention to provide fluorescent dyes and a method of optical pH measurement with the advantages of greater fluorescence, greater stability, lower temperature sensitivity, and larger Stokes shift than heretofore known.

It is yet another object of the invention to provide fluorescent dyes immobilized on a solid support and a method of optical pH measurement therewith.

It is a further object of the invention to provide a fiber optic pH sensor using fluorescent carbazine dyes.

It is a still further object of the invention to provide fluorescent dyes and a method of pH determination wherein all excitation and emission wavelengths are in the visible range so that inexpensive plastic fiber optic materials can be used in a fiber optic pH sensor.

These and other objects are achieved by providing a composition for indicating pH of a solution into which the composition is placed comprising a fluorescent carbazine dye covalently bonded to a solid support, the dye-support composition represented by the formula:

D-B-M wherein M is any solid support containing or derivatized to contain a functional group reactive with hydrazine such that reaction with hydrazine forms a hydrazine-derivatized solid support; D is any fluorescent carbazine dye reactive with the hydrazine-derivatized solid support at the 1-carbon of the spiro ring; and B is the covalent linkage formed by reaction between the hydrazine-derivatized solid support and the 1-carbon of the carbazine dye. The carbazine dye (D) of the composition is represented by the formula

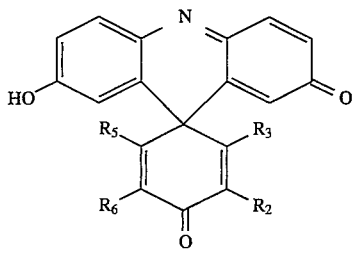

(Formula 1)

wherein $R_2$, $R_3$, $R_5$, and $R_6$ are each independently a member selected from the group consisting of H and alkyl. Preferably, the carbazine dye is a single excitation, dual emission dye. Preferably, B is a covalent linkage selected from the group consisting of —NHNH—, =N—NH—, and =N—N=. Preferably, M is a member selected from the group consisting of periodate-oxidation-susceptible polymers, epoxide-reactive supports, inorganic supports, polyaldehydes, and poly(methyl ketones). Preferred periodate-oxidation-susceptible polymers include paper, starch, cellulose, amylose, rayon, cellophane, and mixtures thereof. Preferred epoxide-reactive supports include supports containing a surface functional group selected from the group consisting of hydroxyl, amino, carboxylic acid, and anhydride. Preferred inorganic supports include glass, glass fibers, sand, silica gel, alumina, titania, nickel oxide, aluminum oxide, zirconia, and mixtures thereof, with glass, glass fibers, sand, silica gel, alumina, and mixtures thereof being more preferred. Preferred polyaldehydes include polyacrolein and polymerized glutaraldehyde.

A composition of matter for use as a pH indicator comprises a fluorescent carbazine dye covalently bonded to hydrazine or a substituted hydrazine, wherein the composition is a member selected from the group consisting of

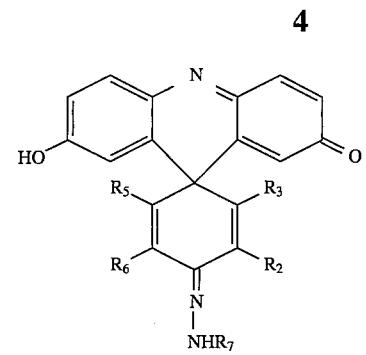

(Formula 3)

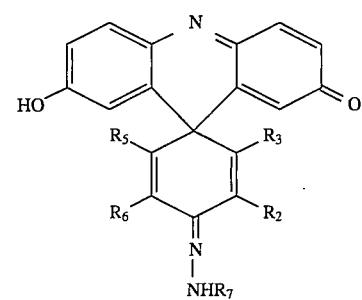

(Formula 4)

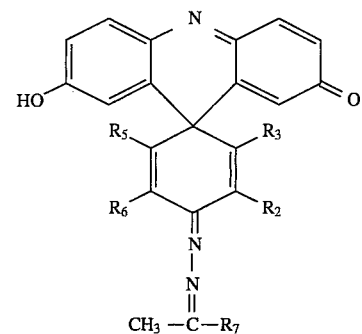

(Formula 5)

wherein $R_2$, $R_3$, $R_5$, and $R_6$ are each selected from the group consisting of H and alkyl, and $R_7$ is selected from the group consisting of H and alkyl. Preferably, the carbazine dye is a single excitation, dual emission carbazine dye.

A fiber optic system for determining pH comprises:

(a) a probe for indicating pH of a solution into which the probe is placed comprising a fluorescent carbazine dye covalently bonded to a solid support, the dye-support composition represented by the formula:

D-B-M wherein M is any solid support containing or derivatized to contain a functional group reactive with hydrazine such that reaction with hydrazine forms a hydrazine-derivatized solid support; D is any fluorescent carbazine dye reactive with the hydrazine-derivatized solid support at the 1-carbon of the spiro ring; and B is the covalent linkage formed by reaction between the hydrazine-derivatized solid support and the 1-carbon of the carbazine dye;

(b) an optical fiber coupled to the probe for receiving excitation light from a fluorometer and conducting the excitation light to said probe and for receiving emitted light from the probe and conducting the emitted light to the fluorometer;

(c) a fluorometer coupled to the optical fiber for generating excitation light at a selected wavelength and delivering the excitation light to the fiber, for receiving and measuring intensities of the emitted light at a first selected wavelength and at a substantially different second selected wavelength and generating an electronic signal containing measurements of the intensities; and (d) means coupled to the fluorometer for receiving the electronic signal, calculating a ratio of the measured intensities, correlating the ratio to a previously determined relationship of such ratios with pH, and displaying the pH.

The fiber preferably comprises a plastic fiber, and the probe is preferably in the form of a bead. The selected wavelength of excitation light is preferably in the range of about 480 to about 540 nm, the first selected wavelength of emitted light is in the range of about 570 to about 620 nm, and the second selected wavelength of emitted light is in the range of about 650 to about 720 nm.

A method of determining pH of a solution comprises the steps of:

(a) providing a composition comprising a fluorescent carbazine dye covalently bonded to a solid support, the dye-support composition represented by the formula:

D-B-M wherein M is any solid support containing or derivatized to contain a functional group reactive with hydrazine such that reaction with hydrazine forms a hydrazine-derivatized solid support; D is any fluorescent carbazine dye reactive with the hydrazine-derivatized solid support at the 1-carbon of the spiro ring; and B is the covalent linkage formed by reaction between the hydrazine-derivatized solid support and the 1-carbon of the carbazine dye;

(b) placing the composition in the solution for which pH is to be determined;

(c) contacting the composition in the solution with light of a selected wavelength for exciting emission of fluorescent light by the carbazine dye;

(d) measuring intensities of the fluorescent light at a first selected wavelength and at a substantially different second selected wavelength;

(e) calculating a ratio of measured intensities at the first selected wavelength and the second selected wavelength; and (f) correlating the ratio with a predetermined relationship of such ratios to pH.

DETAILED DESCRIPTION OF THE INVENTION

Figure 1:
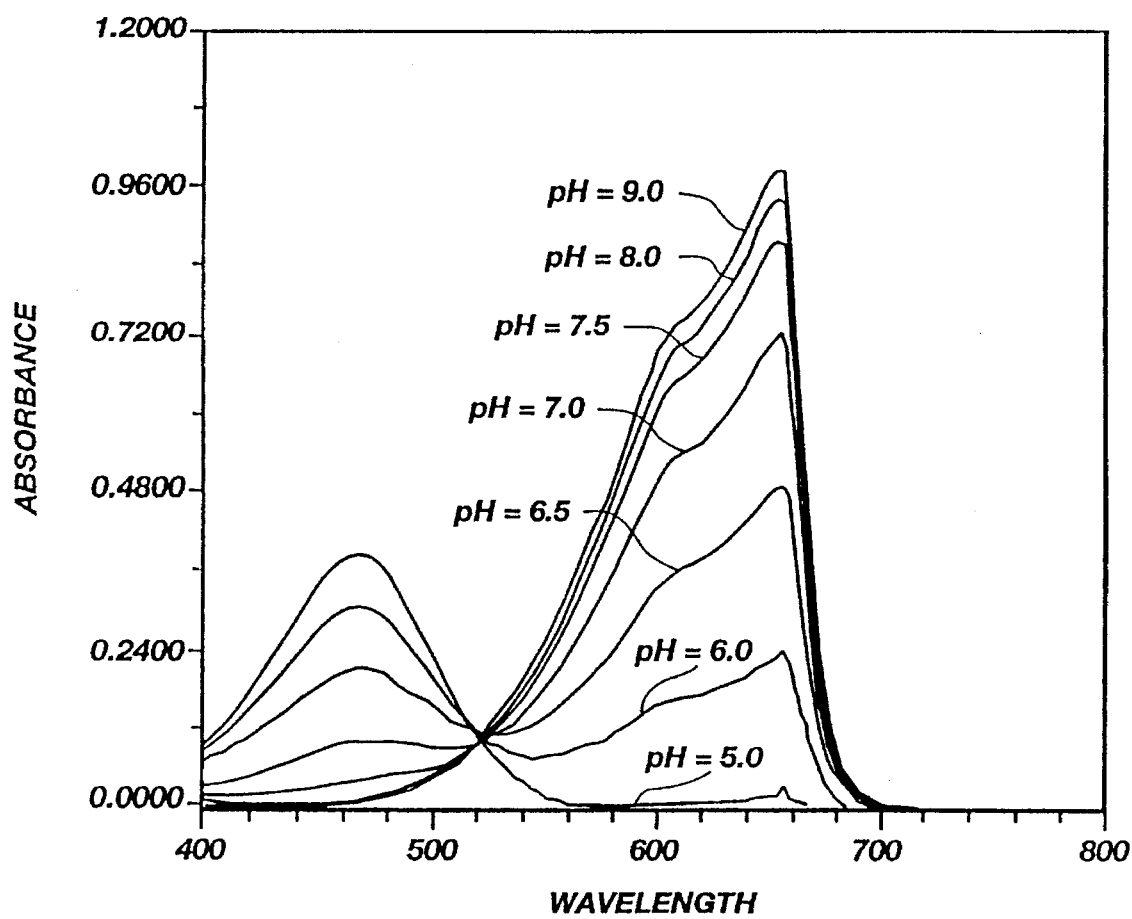
FIG. 1 shows a graphic representation of absorbance of an illustrative carbazine dye at wavelengths in the range of 400–800 nm at various pH levels.

Before the present compositions and methods for carbazine-dye-based pH measurement are disclosed and described, it is to be understood that this invention is not limited to the particular process steps and materials disclosed herein as such process steps and materials may vary somewhat. It is also to be understood that the terminology and examples employed herein are used for the purpose of describing particular embodiments only and are not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a composition containing "a carbazine dye" includes reference to a mixture of two or more such carbazine dyes, reference to "a solid support" includes reference to one or more of such solid supports, and reference to "a functional group" includes reference to a mixture of two or more such functional groups.

In describing and claiming the present invention, the following terminology will be used in accordance with the definitions set out below.

As used herein, "periodate-oxidation-susceptible polymer" means a polymer containing —OH groups attached to adjacent carbon atoms such that upon oxidation with periodic acid the carbon-carbon bond is cleaved and such —OH groups are oxidized to aldehyde groups. Preferred periodate-oxidation-susceptible polymers include paper, starch, cellulose, amylose, rayon, cellophane, and the like and mixtures thereof.

As used herein, "epoxide-reactive support" means a solid support containing a functional group that is reactive with an epoxide resulting in formation of a covalent bond between the solid support and the epoxide. Such functional groups that are reactive with an epoxide include hydroxyl, amine, carboxylic acid, and anhydride groups.

As used herein, "inorganic support" means a solid support that is composed of an inorganic material. Preferred inorganic supports include glass, glass fibers, sand, silica gel, alumina, titania, nickel oxide, aluminum oxide, zirconia, and mixtures thereof. More preferred inorganic supports include glass, glass fibers, sand, silica gel, alumina, and mixtures thereof.

As used herein, "fluorometer" means a device for generating light at a selected wavelength for exciting fluorescence of a carbazine dye, receiving and measuring intensities of fluorescent light emitted by such carbazine dye at a first selected wavelength and at a substantially different second selected wavelength, and generating an electronic signal containing measurements of said intensities.

Carbazine Dyes

A generalized structure for the carbazine dyes of the present invention is shown in the following formula:

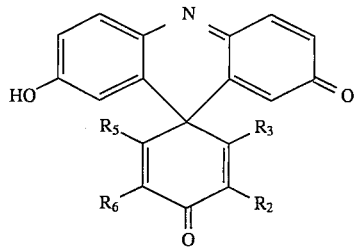

(Formula 1)

wherein $R_2$, $R_3$, $R_5$, and $R_6$ are independently selected from the group consisting of H and alkyl. No dye is formed if $R_2$, $R_3$, $R_5$, or $R_6$ contains an oxygen atom, such as a alcohol, ether, carbonyl, or a halogen atom.

These carbazine dyes are prepared by a modification of the method of R. Hill et al., supra, hereby incorporated by reference, and shown qualitatively in the following reaction scheme.

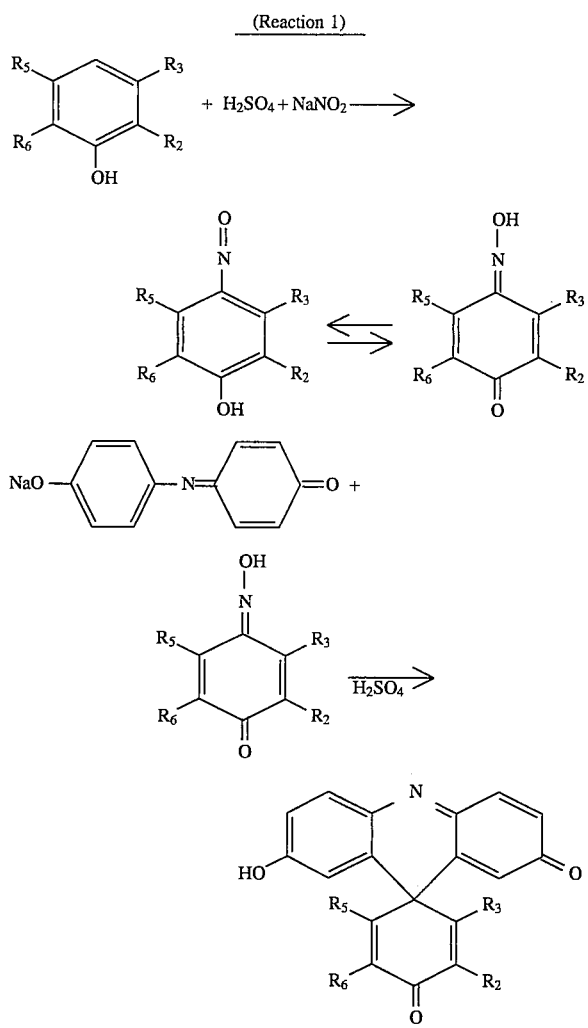

(Reaction 1)

The sodium salt of indophenol is reacted with a substituted phenol that has been modified by reacting with sodium nitrite in sulfuric acid. The modified phenol/indophenol reaction is carried out in 90% sulfuric acid. The reaction mixture is maintained at 40° C. and under slight vacuum to remove nitrogen oxides as the dye is synthesized. Sulfuric acid concentration is critical to the efficiency of the reaction and must be 90%±3% for good yields. Very poor yields result from sulfuric acid concentrations of less than 87% or greater than 93%. Dye formation, fluorescence, and reactivity with a solid support depend on the nature of the substituents on the phenol moiety.

EXAMPLE 1

All reagents used in this and the following examples were purchased from Aldrich Chemical Co. (Milwaukee, Wis.), Sigma Chemical Co. (St. Louis, Mo.), or Spectrum Chemical Co. (Gardena, Calif.), and were used without further purification. One gram of the sodium salt of indophenol was thoroughly mixed with 1.5 g of powdered phenol. This mixture was added to 10 ml of 90.0% sulfuric acid containing 600 mg of dissolved sodium nitrite at 40° C. in a 2000 ml side arm flask containing about 100 ml of 1 cm diameter glass spheres. The top of the flask was then sealed with a stopper and a slight vacuum was applied to aid in removal of nitrogen oxides that formed immediately. The flask and contents were incubated for 15 min at 40° C. with intermittent shaking, and then an additional 10 ml of 90% sulfuric acid containing 600 mg of sodium nitrite was added and mixed with shaking. The top was again sealed, and the flask and contents were incubated another 15 min at 40° C. with occasional shaking. Then, 1 g of powdered phenol was added with shaking. The top was again sealed and the reaction was permitted to proceed for 30 minutes with occasional shaking.

The reaction mixture was then poured into about 2 liters of ice water with mixing. This mixture was then exhaustively extracted with cold diethyl ether. The ether extract was filtered and then extracted with cold 3% sodium carbonate solution. The resulting highly fluorescent carbonate solution was filtered, then a slight current of air was passed through it to remove dissolved ether. Then, 3.5 g of potassium ferricyanide was slowly added to this solution and kept at room temperature for 48 hours. The ferricyanide treatment destroys by-products of the reaction. This solution, containing fluorescent carbazine dye and decomposed impurities, was filtered and then treated with sufficient calcium chloride to precipitate the carbonate. This turbid, yellow-green solution was exhaustively extracted with diethyl ether. At this stage of purification, the ether extract was highly fluorescent orange. This ether solution was then filtered and extracted with 3% carbonate solution. The resulting fluorescent blue carbonate solution was acidified to pH 5 by addition of glacial acetic acid. Upon standing at 5° C. for several hours, the orange-colored solid carbazine dye separated as a fine powder. The solid dye was collected by filtration and dried under vacuum. The resulting carbazine dye was 7-hydroxyspiro[acridine-9,1'-cyclohexa-2',5'-diene]-2(9H),4'-dione having the structure of Formula 1 wherein $R_2$, $R_3$, $R_5$, and $R_6$ were each H.

EXAMPLE 2

The procedure of Example 1 was followed with the exception that 3,5-dimethylphenol (3,5-xylenol) was substituted for phenol. The resulting carbazine dye had the structure of Formula 1 wherein $R_2$ and $R_6$ were H and $R_3$ and $R_5$ were methyl.

EXAMPLE 3

The procedure of Example 1 was followed with the exception that 2,3,5-trimethylphenol (isopseudocumenol) was substituted for phenol. The resulting carbazine dye had the structure of Formula 1 wherein $R_6$ was H and $R_2$, $R_3$, and $R_5$ were methyl.

EXAMPLE 4

The procedure of Example 1 was followed with the exception that durenol (2,3,5,6-tetramethylphenol) was substituted for phenol. Durenol was synthesized by exhaustive methylation of 3,5-dimethylphenol (3,5-xylenol) by the method of Burawoy, J. Chem. Soc. 400 (1944), hereby incorporated by reference. The resulting carbazine dye had the structure of Formula 1 wherein $R_2$, $R_3$, $R_5$, and $R_6$ were each methyl.

EXAMPLE 5

The procedure of Example 1 was followed with the exception that 5,6,7,8-tetrahydro-1-naphthol was substituted for phenol. The resulting carbazine dye had the structure of Formula 1 wherein $R_2$ and $R_3$ were 2,3-cyclohexyl and $R_5$ and $R_6$ were each H.

EXAMPLE 6

The procedure of Example 1 was followed with the exception that 5-isopropyl-3-methylphenol was substituted for phenol. The resulting carbazine dye had the structure of Formula 1 wherein and $R_6$ were H, $R_3$ was isopropyl, and $R_5$ was methyl.

EXAMPLE 7

The procedure of Example 1 was followed with the exception that o-tert-butylphenol was substituted for phenol. The resulting carbazine dye had the structure of Formula 1 wherein $R_3$, $R_5$, and $R_6$ were each H and $R_2$ was t-butyl.

EXAMPLE 8

The procedure of Example 1 was followed with the exception that m-tert-butylphenol was substituted for phenol. No detectable amount of carbazine dye was synthesized. It is thought that steric hindrance prevented reaction of the substituted phenol with indophenol.

EXAMPLE 9

Figure 2:
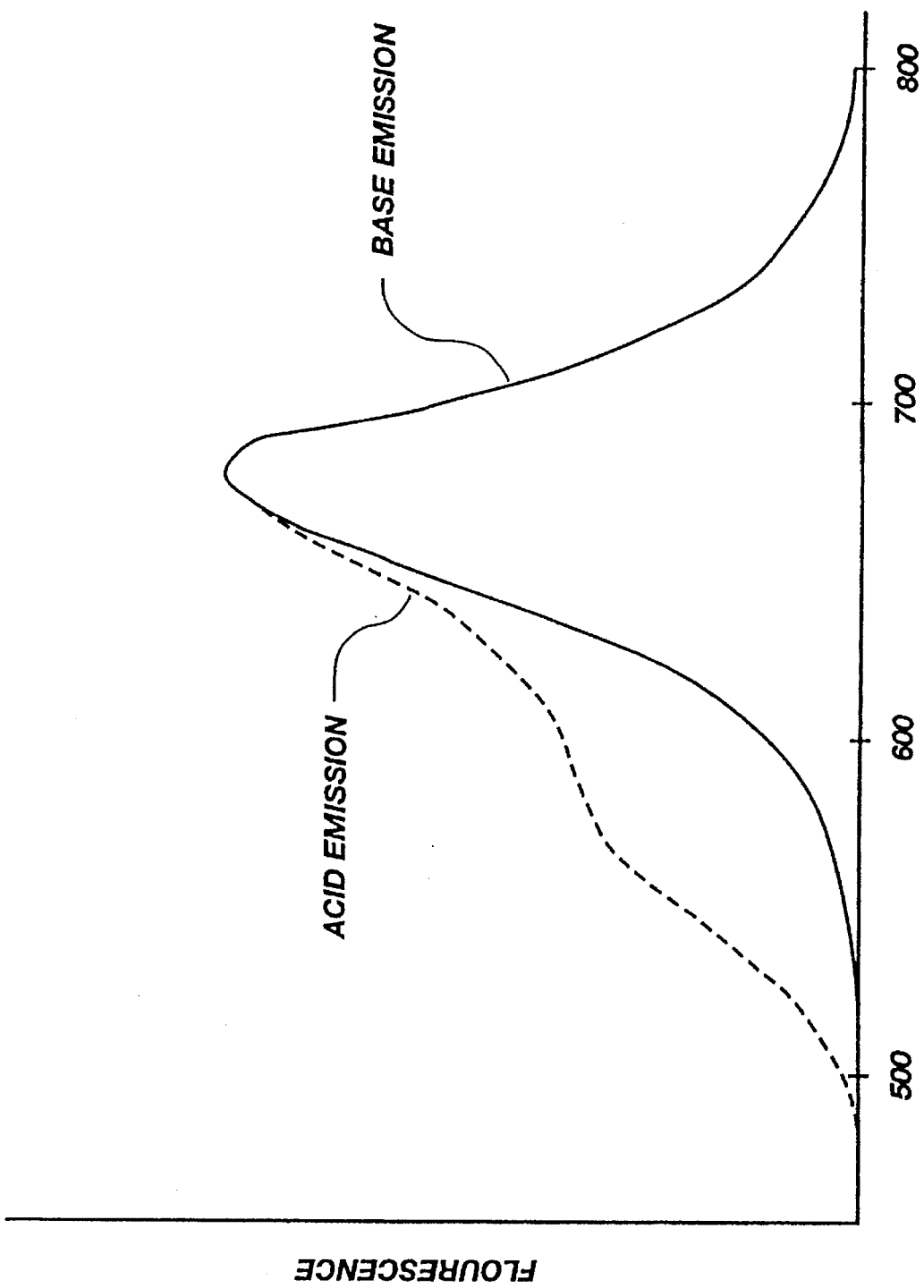
FIG. 2 shows a graphic representation of fluorescence emission of acid and base forms of an illustrative carbazine dye at wavelengths in the range of about 500–800 nm.

Certain properties of the carbazine dyes of Examples 1–7 were determined. Spectral data were obtained either with a Hewlett Packard Model 8452A Diode Array Spectrophotometer or a Perkin Elmer Model LS 50B Luminescence Spectrometer. All of the dyes are similar in their absorbance and emission spectra, with only slight differences in peak locations, ratios of absorbance of acid to absorbance of base, and $pK_a$s. A typical absorbance curve versus pH is shown in FIG. 1. The unmodified dyes show large separation between absorbance peaks for acid and base forms. Typically, the acid form has a peak absorbance at about 480 nm, and the base form has a peak absorbance at about 660 nm. A typical fluorescence emission curve of both acid and base forms of the dyes is shown in FIG. 2. Fluorescence emission of the base form has a well-defined single peak at approximately 690 nm. The acid form of the dyes exhibits an emission spectrum similar to that of the base form, but has a definite shorter wavelength emission component near 600 nm.

The $pK_a$ values, i.e. the approximate pH values of an aqueous solution of the dye where the acid and base forms of the dye are present in equal concentrations, were derived from the absorbance spectra and are listed in the Table below. As mentioned above, indicator dyes are generally most sensitive to pH changes near their $pK_a$s.

The relative susceptibilities of the dyes to immobilization on a solid support were determined from the intensity of dye covalently bound to regenerated cellulose dialysis membrane. The immobilization data summarized in the Table below were taken from measurements in 2% carbonate solution normalized to an arbitrary scale of 1 to 10, where 1 represents no detectable amount of dye bound and 10 represents the greatest quantity of dye bound. The conditions of coupling of the dyes to the regenerated cellulose were according to immobilization Method 2 described below. Carbazine dyes immobilized under these conditions yield a uniform fluorescent blue dialysis membrane that changes to fluorescent orange upon acidification. As a point of reference, the carbazine dye of Example 3 immobilized on a "SPECTRAPOR 1" membrane (molecular weight cutoff 6000 to 8000) yields a blue membrane with an absorbance at 660 nm of greater than 1 at pH>9.

The fluorescence ratings shown in the Table are based on the maximum fluorescence obtainable from an aqueous carbazine dye solution with excitation at the maximum absorbance wavelength for the particular dye, but with concentrations and pH constant between all dyes. The fluorescence rating does not change with pH, i.e. the dyes that are most fluorescent in base are also most fluorescent in acid. Quantum yields of the acid forms of the dyes appears as high as the base forms. The carbazine dye of Example 4, sold commercially as "CARBAZINE 720" (Exciton, Inc., Dayton, Ohio), has a quantum yield of approximately 50% in aqueous solution containing base. The carbazine dye of Example 3 is as fluorescent, can be produced in higher yield, and has a higher immobilization efficiency than "CARBAZINE 720."

Properties of the carbazine dyes of Examples 1–7 are summarized in the following Table:

TABLE

| Dye[a] | Yield[b] | Absorb. Ratio[c] | $pK_a$ | Immobilization[d] | Fluorescence[d] |
|---|---|---|---|---|---|
| 1 | high | 0.426 | 6.5 | 10 | 2 |
| 2 | low | 0.391 | 6.5 | 6 | 7 |
| 3 | 18% | 0.380 | 6.5 | 6 | 10 |
| 4 | 15% | 0.388 | 6.5 | 4 | 10 |
| 5 | 10% | 0.387 | 6.7 | 6 | 8 |
| 6 | 10% | 0.377 | 6.4 | 6 | 7 |
| 7 | low | 0.324 | 7.2 | 1 | 6 |

[a]The number of the dye refers to the Examples.
[b]Based on the molar ratio of dye synthesized to indophenol.
[c]Absorbance ratio of acid/base.
[d]Relative scale of 1 to 10 where 10 is best.

These data suggest that for high fluorescence efficiency, some substitution in the spiro ring is required. The chromophore portion of the dye molecule comes from the indophenol molecule, which is virtually nonfluorescent. It has been suggested that the fluorescence of carbazine dyes is derived from the tetrahedral carbon bridge causing the indophenol chromophore to be rigid. Since all of the dyes presented in the Table contain the tetrahedral carbon bridge, substitution in the spiro ring appears to play an important part in fluorescence.

The results presented in the Table also show a trend relating immobilization efficiency to steric effects near the 1 position of the spiro ring. The dye of Example 7, containing a t-butyl group for $R_2$, does not react to any detectable extent in any of the immobilization schemes disclosed herein, presumably due to steric effects near the binding site to the solid support. The dye of Example 4, further, does not bind as effectively as does the dye of Example 3, presumably due to the presence of a methyl group for $R_6$. Finally, the best dye for binding to a solid support in terms of immobilization efficiency is the unsubstituted dye of Example 1.

The optimum carbazine dye for pH measurement applications is a compromise between yield, fluorescence, and immobilization efficiency, each of which is affected by the substituents on the spiro ring. The dye of Example 3 is a preferred carbazine dye for pH measurement because it represents an effective compromise of the various factors that influence pH measurement when immobilized on a fiber optic probe.

Modification of Carbazine Dyes

The spiro ring of some of the carbazine dyes described herein are reducible by nickel/aluminum alloy in aqueous sodium hydroxide to the compounds shown generically in the following formula:

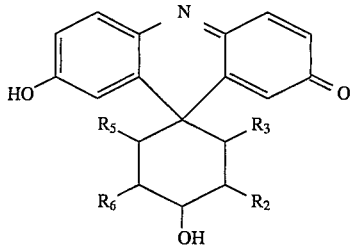

(Formula 2)

wherein $R_2$, $R_3$, $R_5$, and $R_6$ are independently selected from the group consisting of H and alkyl. These saturated compounds exhibit similar absorption and emission spectra to the corresponding unsaturated compounds with the exception of the absorption maxima for the basic forms of the molecules. The basic forms of the saturated compounds all show a blue shift of approximately 30 nm (from 660 nm to 630 nm) for the absorption peak.

EXAMPLE 10

The carbazine dye of Example 1 was reduced according to the following procedure. Approximately 100 mg of dye was dissolved in 20 ml of 1N NaOH in a beaker fitted with a vacuum port. Approximately 500 mg of 50% nickel/ aluminum alloy was added, then the beaker was sealed and immediately placed under vacuum. After a few minutes, the blue dye solution became colorless as the leuco compound formed. After a few minutes more, gas bubbles began to form as hydrogen evolved by the action of the base on the aluminum. After an additional several minutes, the vacuum was removed, and the mixture was rinsed from the beaker into approximately 500 ml of 0.1N sodium bicarbonate. This solution was filtered several times to remove aluminum hydroxide and the remains of the alloy. Air was slowly bubbled through the filtered solution, containing the dissolved dye, to oxidize the leuco compound. As this occurred, the fluorescent color returned. This solution was then treated with sodium phosphate until a yellow-green color was obtained, and was then extracted with cold ether. The ether extract was filtered, and then extracted with cold 3% carbonate solution. Air was then bubbled through the fluorescent blue carbonate solution to remove the ether and then was acidified to pH 5 with glacial acetic acid. The acidified solution was chilled for several hours at 5° C., and then the precipitated reduced dye was collected by filtration and dried under vacuum. The resulting reduced carbazine dye had the structure according to Formula 2 wherein $R_2$, $R_3$, $R_5$, and $R_6$ are each H.

Immobilizing Carbazine Dyes on Solid Supports

Carbazine dyes according to the present invention bind to hydrazine derivatives to form the compounds shown in the following formulas:

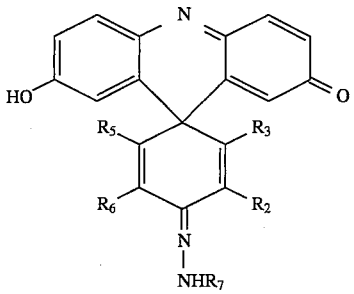

(Formula 3)

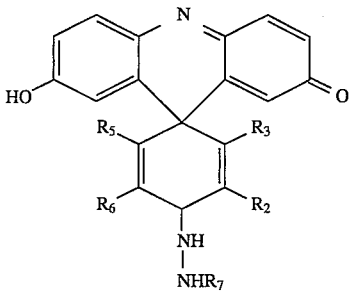

(Formula 4)

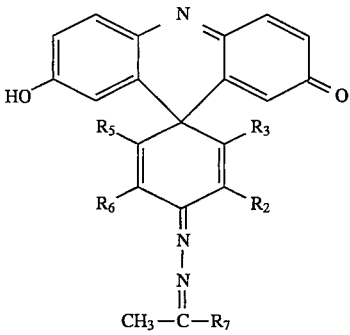

(Formula 5)

wherein $R_2$, $R_3$, $R_5$, and $R_6$ are independently selected from the group consisting of H and alkyl, and $R_7$ is a member selected from the group consisting of H and alkyl. Hydrazine and its derivatives react according to the following reaction scheme in anhydrous protic or aprotic solvents or in aqueous solution to form carbazine imines as shown in Formula 3:

(Reaction 2)

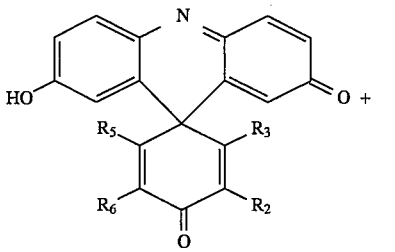

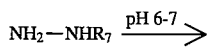

-continued
(Reaction 2)

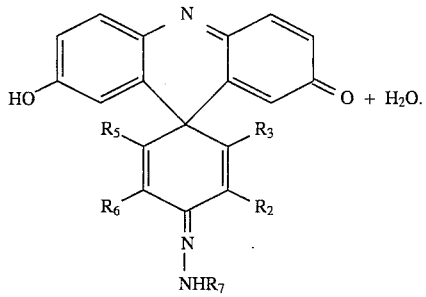

+ H₂O.

These reactions occur best at between about pH 6.0 and 7.0, or simply in aqueous solution at a pH where the carbazine dye remains green in color. The base form of a carbazine dye is bright blue, whereas the acid form is yellowish orange. At the $pK_a$ of the dye, about pH 6.5, there are equal numbers of molecules of ionized (basic form, blue) and unionized (acid form, yellow) dye molecules, thus resulting in a green to blue green color. Substituted hydrazines are more reactive in coupling to carbazine dye than is free hydrazine.

Carbazine imines, although not particularly stable, are reducible to stable carbazine-substituted hydrazines, as shown in Formula 4, by sodium cyanoborohydride, as shown in the following reaction scheme:

(Reaction 3)

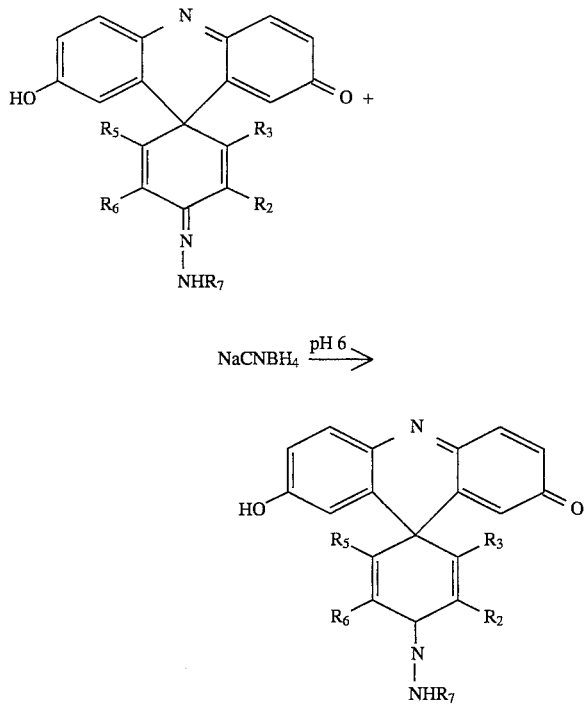

This reaction may be carried out simultaneously with the imine formation reaction as a "one pot" reaction. Carbazine dye, hydrazine or substituted hydrazine, and sodium cyanoborohydride are dissolved or suspended in water at pH 6.2. Cyanoborohydride is known to rapidly and selectively reduce imine groups under these conditions, and is relatively stable in aqueous solutions above pH 6.0.

Carbazine-substituted hydrazines are highly fluorescent compounds with spectra and $pK_a$s similar to the free dyes. The covalent bond formed between the carbazine dye and the substituted hydrazine is chemically stable, and the substituted hydrazine can be part of an insoluble support. Thus, carbazine dyes can be covalently bonded to hydrazine-modified supports.

Carbazine azines, shown generically in Formula 5, are prepared according to the following reaction scheme:

(Reaction 4)

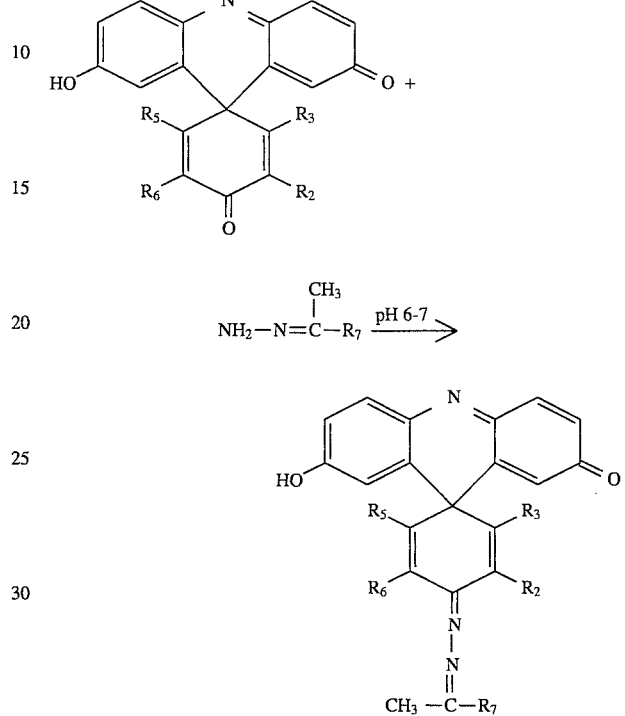

These compounds readily form in aqueous or organic solution with wide latitude in reaction conditions. The best coupling, however, seems to be in aqueous solution at a pH of about 6.0 to 6.5.

Figure 3:
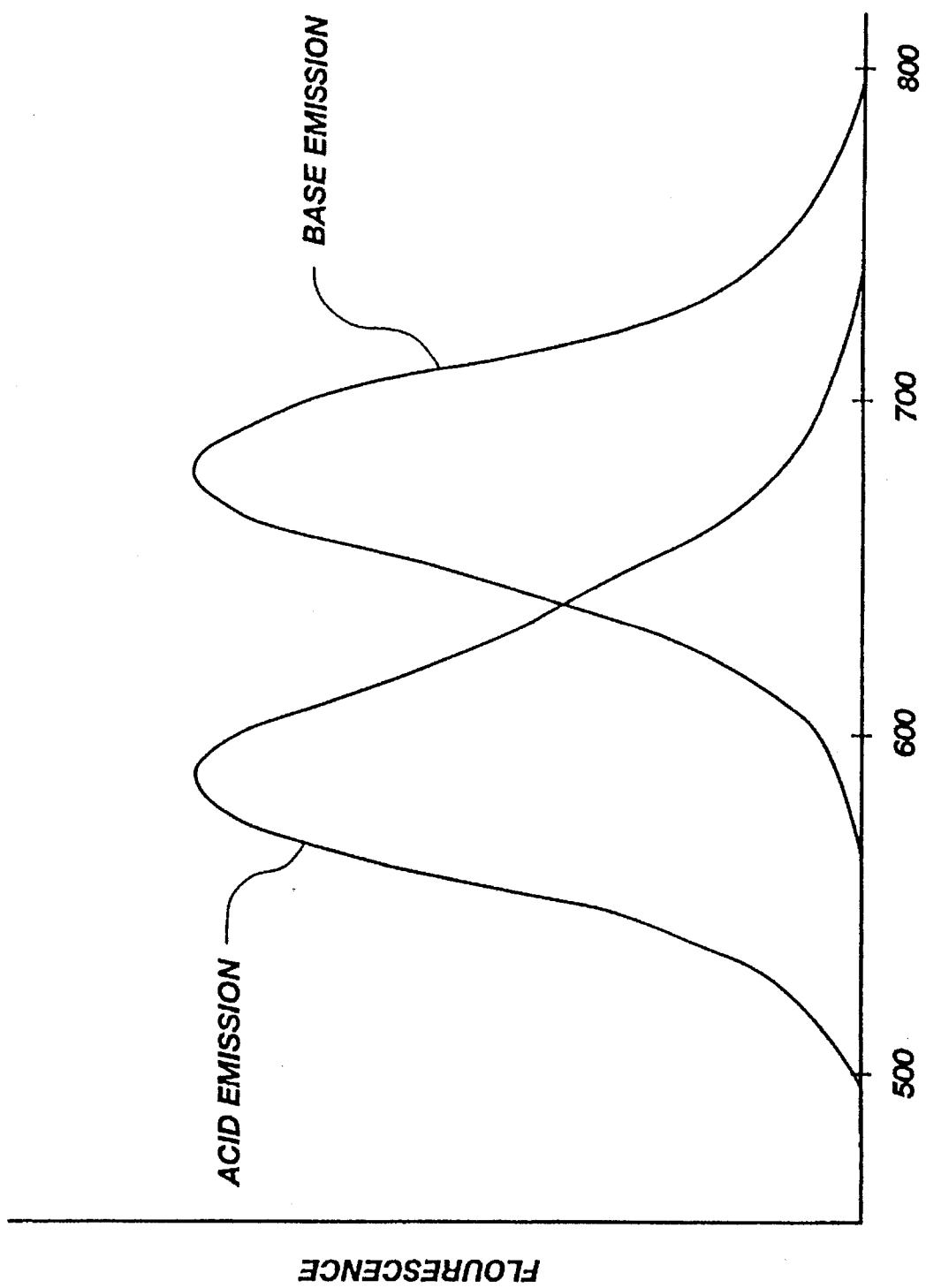
FIG. 3 shows a graphic representation of fluorescence emission of acid and base forms of a carbazine azine at wavelengths in the range of about 500–800 nm.

Carbazine azines show unique fluorescence behavior compared to other carbazine derivatives. While absorbance data remain essentially unchanged, emission spectra are as shown in FIG. 3. Further, the $pK_a$ of these compounds is about 1 pH unit higher, i.e. about pH 7.5, than the unmodified dye. Base form emission remains unchanged, but acid form emission is in a well resolved, single peak centered around 590 nm. Carbazine azines, thus, are dual excitation, dual emission dyes with acid form excitation/emission of 480 nm/590 nm and base form excitation/emission of 660 nm/690 nm. The acid/base absorbance curves cross, as shown in FIG. 1, at approximately 520 nm. An excitation wavelength can be selected to suitably excite both the acid and base forms of the carbazine azine to produce a single excitation, dual emission pH indicator. As with the other dye forms, the carbazine azine is highly fluorescent and chemically stable.

In the following methods, "R" is used to represent the solid support onto which the carbazine dye is to be immobilized. In some instances the solid support may be modified, derivatized, or functionalized according to the reaction schemes that follow. It is to be realized that there must necessarily be some functional group or groups on the solid support for a chemical reaction to occur. These groups can be in the form of —OH, =O, —NH₂, —MgX, —COOH, ketones, and so forth, that can then be further reacted by oxidation to aldehydes or acids, derivatized with glycidol, GOPS, or reacted directly with hydrazine or hydrazine derivative according to the reaction schemes that follow. However, for purposes of clarity and uniformity, the solid support will be simply referred to as "R." It will be clear to one skilled in the art what "R" represents according to the reaction scheme utilized.

Polysaccharide Supports—Method 1

In a first method, the dye—reactive hydrazine/hydrazone groups are readily incorporated onto the surface of a periodate-oxidation-susceptible polymer support, such as paper, starch, cellulose, amylose, rayon, cellophane, and the like and mixtures thereof. Upon treatement with periodic acid, compounds containing —OH groups attached to adjacent carbon atoms undergo oxidation with cleavage of carbon-carbon bonds. R. Morrison & R. Boyd, *Organic Chemistry* 523–24 (4th ed., 1983). The —OH groups are oxidized to aldehyde groups. The aldehyde groups of the oxidized polysaccharide are then reacted with hydrazine in the presence of sodium cyanoborohydride to form an immobilized hydrazine. This hydrazine-modified support is then reacted with a carbazine dye as described above. This method results in some polymer degradation due to breaking of the carbon-carbon bonds by periodate oxidation of the polymer chain. This reaction scheme is illustrated as follows:

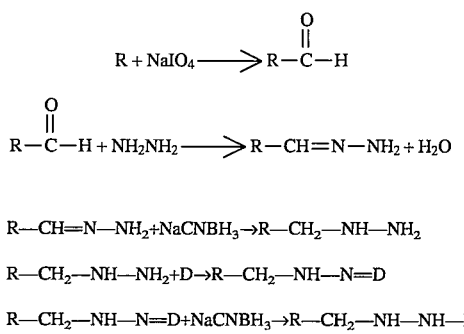

wherein R is a member selected from the group consisting of paper, starch, cellulose, amylose, rayon, cellophane, and other polymers that can be oxidized by periodate to yield an aldehyde group and D is a carbazine dye according to Formula 1 with $R^2$, $R^3$, $R^5$, and $R^6$ independently selected from H and alkyl. The covalent bonds between the carbazine dye and the substituted hydrazine are formed according to Formulas 3 and 4.

Polysaccharide Supports—Method 2

A second method of immobilizing carbazine dyes on polymer supports does not require polymer degradation, i.e. breaking of carbon-carbon bonds of the polymer by periodate oxidation, and produces substantially higher yields of immobilized dye than Method 1. This second method is functional with any support material that contains an epoxide-reactive group, such as a hydroxyl group, amine group, carboxylic acid group, or anhydride group. Reactions of various epoxide-reactive groups with the epoxide, glycidol, are illustrated as follows:

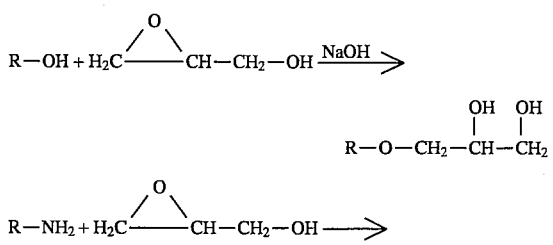

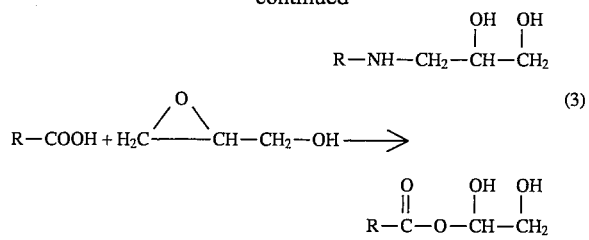

wherein R represents the solid support exclusive of the epoxide-reactive group.

Glycidol reacts with the epoxide-reactive group of the solid support, usually in an aqueous solution with either acid or base catalysis, to form a poly-substituted product. The vicinal hydroxyls, i.e. hydroxyl groups on adjacent carbon atoms, of the glycidol residue are selectively oxidized by periodate to the polyglyoxal (polyaldehyde) form, which is sequentially reacted with hydrazine and a carbazine dye as in the first method described above. These reactions are illustrated in the following reaction scheme:

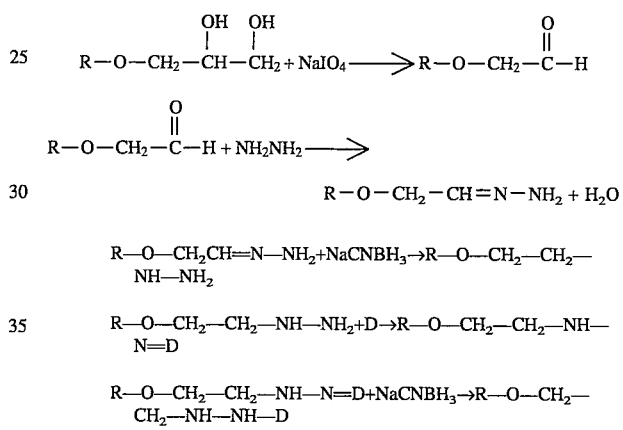

wherein R is the solid support containing the epoxide-reactive group and D is a carbazine dye according to Formula 1 with $R^2$, $R^3$, $R^5$, and $R^6$ independently selected from H and alkyl. The covalent bonds between the carbazine dye and the substituted hydrazine are formed according to Formulas 3 and 4.

Inorganic Supports—Method 3

Many inorganic supports are "silanized" by treatment with a silanizing reagent. These reactions are generally thought to result in an organic molecule covalently attached to a silanol (Si—OH) surface functionality. This treatment both blocks the reactivity of the surface silanol functionality and imparts a reactive functionality to the surface of the inorganic support corresponding to the organic portion of the silanizing reagent.

Glycidoxypropyl trimethoxysilane (GOPS) reacts with inorganic supports such as glass, glass fibers, sand, silica gel, alumina, titania, nickel oxide, aluminum oxide, zirconia, and other hydrophilic inorganic supports and mixtures thereof to produce an organic epoxy functionality on the inorganic surface, as is illustrated in the following reaction scheme with silica gel:

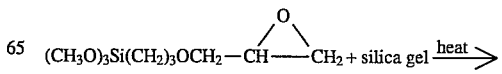

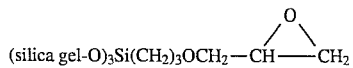

This epoxy functionality can be acid hydrolyzed to yield a surface containing vicinal hydroxyl groups. These vicinal hydroxyl groups can be further oxidized by periodate to produce a surface aldehyde functionality. These reactions are illustrated as follows:

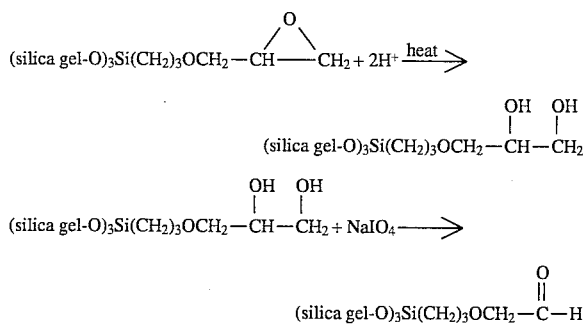

The surface aldehyde group can be coupled sequentially to hydrazine and a carbazine dye as described above.

Inorganic Supports—Method 4

Glycidol will react with the vicinal hydroxyl groups present on the compound of Method 3 resulting from the reaction of silica gel or other appropriate inorganic support to result in a periodate-oxidizable surface of greater hydrazine binding capacity, as follows:

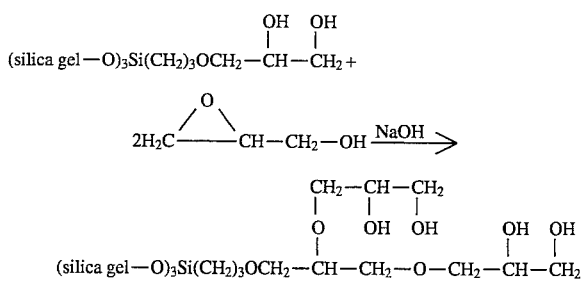

The vicinal hydroxyl groups can then be oxidized with periodate to yield aldehyde groups, which can then be sequentially coupled to hydrazine and a carbazine dye as described above.

Polyaldehyde Supports—Method 5

Polyaldehydes, such as polyacrolein and polyglutaraldehyde, react with hydrazine in the presence of cyanoborohydride to yield substituted polyhydrazine materials. Carbazine dyes can then be bonded to the polyhydrazine supports according to the procedure of Method 1. Reaction of the polyaldehydes with hydrazine is illustrated as follows:

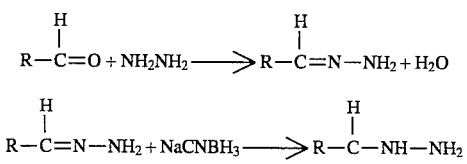

Ploymethylketone Supports—Method 6

Polymethylketones undergo a substitution reaction with hydrazine hydrate at elevated temperatures to yield polymethyl hydrazone. This product reacts directly with carbazine dyes to produce highly fluorescent azine polymers with unique optical and chemical characteristics for pH measurement. Reactions of polymethylketones with hydrazine and of polymethyl hydrazone with carbazine dye are illustrated as follows:

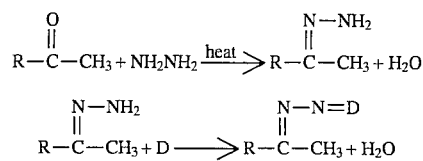

EXAMPLE 17

Approximately 1 g of microcrystalline cellulose was suspended in 50 ml of 1N $NaIO_4$ solution and reacted for 1 hour at room temperature. The cellulose was removed by filtration, washed extensively with water and then with anhydrous ethanol, and then dried under vacuum. The cellulose was then suspended in a 10% (v/v) aqueous solution hydrazine hydrochloride, pH 6.2, for 5 hours at room temperature. The cellulose was then again removed by filtration, washed extensively with water, and then suspended in a solution of about 1 mg/ml sodium cyanoborohydride in water, pH 6.2, and reacted for 5 hours at room temperature. The cellulose was then again removed by filtration, washed extensively with water and then with anhydrous ethanol, and then dried under vacuum. The resulting compound was a hydrazine-modified cellulose support prepared according to Method 1.

EXAMPLE 18

About 1 g of microcrystalline cellulose was suspended in about 20 ml of a 10% (w/v) solution of glycidol in 1N sodium hydroxide and permitted to react overnight at room temperature. The solid material was separated by filtration, washed extensively with water and ethanol, and then reacted sequentially with periodate, hydrazine, and sodium cyanoborohydride according to the procedure of Example 17.

EXAMPLE 19

About 1 g of silica gel was heated to 90° C. in 50 ml of a 10% (w/v) of GOPS and maintained for 1 hour while the pH was maintained between 1 and 2 by addition of HCl. The modified silica gel was then collected by filtration, washed extensively in water, and then reacted sequentially with periodate, hydrazine, and sodium cyanoborohydride according to the procedure of Example 17.

EXAMPLE 20

About 1 g of glass fibers was reacted with GOPS according to the procedure of Example 19, and then rinsed extensively. The modified glass fibers were then reacted sequentially with glycidol, periodate, hydrazine, and sodium cyanoborohydride according to the procedure of Example 18.

EXAMPLE 21

About 1 g of polyacrolein was reacted with hydrazine and cyanoborohydride according to the procedure of Example 17.

EXAMPLE 22

In this example, 5.0 g of poly(methyl vinyl ketone) was suspended in about 50 ml of hydrazine hydrate and heated in a steam bath for 48 hours. The swollen, cross-linked gel was then removed by filtration and washed extensively with water. The resulting gel was a hydrazone-containing support.

EXAMPLE 23

Coupling of Carbazine Dye to Hydrazine-modified Support.

About 1 g of hydrazine-modified support prepared according to the procedure of Example 17 was suspended in 1 ml of 0.1N [N-(2-acetamido)-2-aminoethane sulfonic acid] (ACES) buffer, pH 6.2. A solution of 5 mg of carbazine dye, prepared according to the procedure of Example 3, dissolved in 200 µl of dimethylformamide was added to the support-containing solution, mixed, and permitted to react overnight at room temperature. The support was then separated by filtration, washed extensively with water, and suspended in 5 ml of ACES buffer, pH 6.2, containing approximately 10 mg of sodium cyanoborohydride. The reaction was permitted to proceed for 5 hours. Since this reaction consumes hydrogen ions, acetic acid was added occasionally to maintain the pH. Upon termination of the reaction, a few drops of aqueous formaldehyde were added to block any unreacted hydrazine groups, followed by addition of about 5 mg more cyanoborohydride to effect the formaldehyde reaction. This blocking reaction was permitted to occur for 1 hour at room temperature.

The two steps of (a) attachment of the carbazine dye to the hydrazine to form a hydrazone, and (b) reduction of the hydrazone with cyanoborohydride to form the dye-substituted hydrazine can also effectively be carried out simultaneously in a one-step reaction. Since the dye is the most valuable reagent in this synthesis, however, it is advantageous to be able to recover the unreacted dye for recycling. The two-step process allows for recovery of the dye without contamination with cyanoborohydride.

EXAMPLE 24

About 1 g of moist hydrazone-containing support, prepared according to the procedure of Example 22, was suspended in 1 ml of ACES buffer, pH 6.2. A solution of 5 mg of carbazine dye, prepared according to the procedure of Example 3, dissolved in 200 µl of dimethylformamide was added to the support-containing solution, mixed, and heated in a steam bath for 1 hour. The support was collected by filtration, washed sequentially with water, acetone, dilute acetic acid, and aqueous carbonate, then stored in water. Dye-substituted azines are chemically stable and require no sodium cyanoborohydride reduction.

Fiber Optic pH Sensor

Fiber optic pH sensors using the materials and methods described herein operate as single excitation, dual emission sensors with excitation between about 480 and 540 nm, acid form emission at about 590 nm, and base form emission at about 690 nm. A ratiometric technique for determining pH with these fiber optic pH sensors comprises exciting the fluorescent dye with a single wavelength of light and simultaneously monitoring fluorescence from the acid form and the base form of the dye. The ratio of emission of the acid form to emission of the base form correlates favorably with pH. The carbazine dyes described herein show less sensitivity to temperature and solvent changes than currently employed fluorescent pH indicators. These fiber optic sensors and method of use eliminate most of the problems heretofore encountered in fiber-optic-based pH measurement systems. Also, the compositions and methods described herein permit the use of inexpensive plastic fiber optic materials, since all wavelengths of light, both excitation and emission, are in the visible part of the spectrum. Most currently used dyes for fiber optic pH measurement require ultraviolet excitation, thereby requiring the use of quartz optical fibers.

To demonstrate the utility of these materials as pH indicators, a fiber-optic-based pH probe was constructed from a fluorescent dye, prepared according to Example 3, bound to a 0.012 inch diameter ketone-containing polyacrylate bead (XAD-7, Rohm & Haas) by the procedure of Example 24 and 0.010 inch plastic optical fiber (Polyoptical 1610 fiber). The bead was glued onto the end of the fiber, without any end polishing or other preparatory steps, with Norland Optical Adhesive #68. This probe was optically coupled to a pulse fiber fluorometer with excitation centered at about 520 nm, acid emission centered at about 600 nm, and base emission centered at about 680 nm. Interference filters were used with bandwidths of about 40 nm to take advantage of the large spectral separation of the dye. The fluorometer was coupled to a computerized data acquisition system for electronic data collection.

Figure 6:
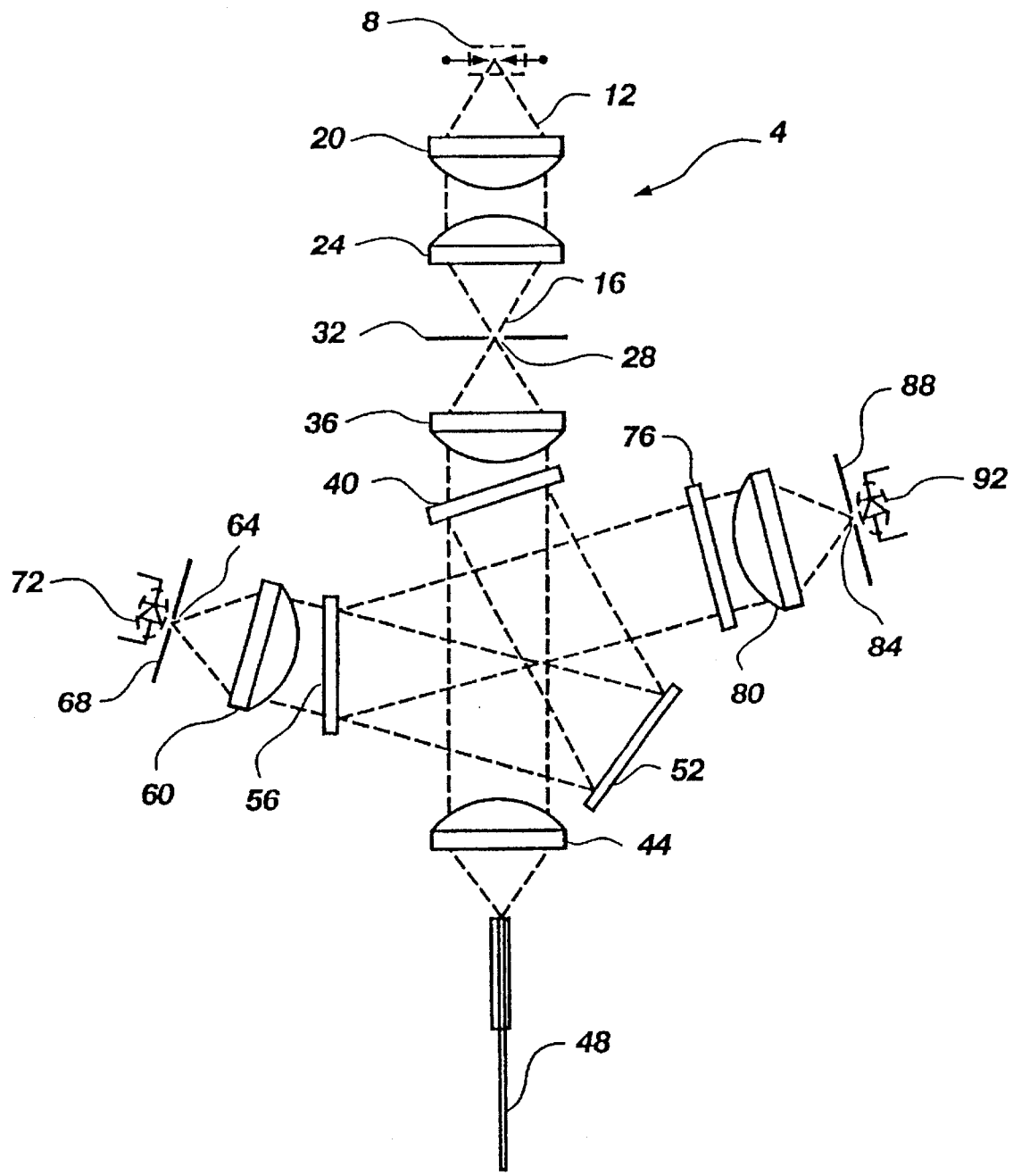
FIG. 6 shows a schematic diagram of an optical system of an illustrative fluorometer for use in determining pH according to the present invention.
Figure 7:
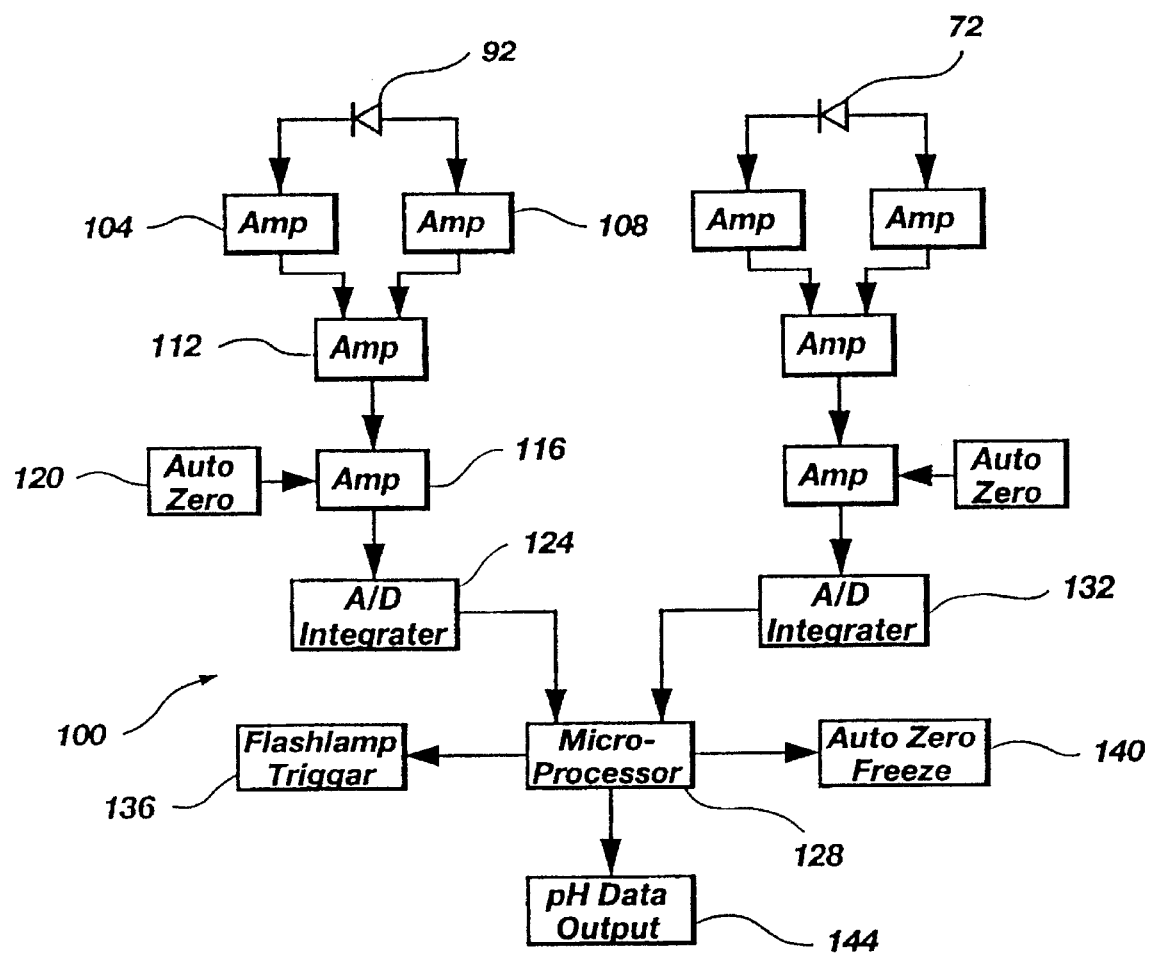
FIG. 7 shows a block diagram of an electronic system of an illustrative fluorometer for use in determining pH according to the present invention.

An illustrative pulse fiber fluorometer that can be used in conjunction with the carbazine dyes of the present invention for measuring fetal pH is disclosed in FIGS. 6 and 7. In FIG. 6 there is shown an optical system 4 for producing an excitation wavelength centered at 520 nm and for detecting emission wavelengths centered at 600 nm and 680 nm. The optical system comprises a flashlamp 8 for generating a high intensity beam 12 of white light. The lamp 8 is selected for a long useful life, e.g. 10 million flashes. Each flash lasts about 100 microseconds. The electrical drive for the lamp 8 is designed to minimize electrical interference with the other electronics.

The beam 12 of white light from each flash is collected and focused to a focal point 16 by lenses 20 and 24. These lenses are aspheric to efficiently collect as much light as possible. The focused light thus formed is used to illuminate pinhole 28 in plate 32. The pinhole 28 has an approximate diameter of 0.060 inch. The focused light can illuminate a substantially larger area than the size of the pinhole 28, thus allowing for some misalignment of the flashlamp 8, lenses 20 and 24, and pinhole 28.

The beam 12 of light passing through the pinhole 28 is collimated by lens 36. The collimated light then passes through filter 40. It is important to achieve good collimation for filter 40 to perform correctly, as will now be explained. Filter 40 is a highly selective interference filter that transmits light of 520 nm±20 nm. Any light that gets through filter 40 in wavelengths at which fluorescence will be measured, 600 nm and 680 nm, will be false fluorescence. The high selectivity needed to substantially eliminate false fluorescence can be achieved only with well collimated light from lens 36.

The light transmitted through filter 40, e.g. 520 nm light, then contacts lens 44, which focuses this light on optical fiber 48. Optical fiber 48 conducts the 520 nm light to a pH indicator probe comprising a fluorescent carbazine dye covalently bonded to a solid support, as has been thoroughly explained above. Upon being illuminated by the 520 nm light, the probe fluoresces with dual emission fluorescence with wavelengths centered at about 600 nm and 680 nm. A portion of this emitted light is gathered by the optical fiber 48, which conducts such emitted light back to the optical system 4 of the fluorometer.

The fluorescent emitted light from the optical fiber 48 passes through lens 44 and from there to filter 40. Filter 40 reflects this emitted fluorescent light to mirror 52. Light contacting mirror 52 is then reflected to filter 56. Filter 56 is another high performance interference filter that transmits light of 680 nm and reflects light of 600 nm wavelength. This transmitted light contacts lens 60, which focuses the 680 nm light onto pinhole 64 in plate 68. This pinhole 64 spatially removes scattered and stray light, since only light emitted from the optical fiber 48 is focused thereon. The focused 680 nm wavelength light that passes through pinhole 64 contacts photodiode 72.

Light reflected by filter 56 contacts filter 76, which is another high performance interference filter that permits only light of about 600 nm to pass therethrough. Such 600 nm light passing through filter 76 then contacts lens 80, which focuses this 600 nm light on pinhole 84 in plate 88. As with pinhole 64, pinhole 84 spatially removes scattered and stray light. The 600 nm light passing through the pinhole 84 then contacts photodiode 92, which detects this 600 nm light.

The angles of filter 40 and filter 56 are maintained at 15 degrees from normal incidence. This angle must be kept small for filter 40 and filter 56 to function properly in transmitting the selected wavelengths of light and reflecting other wavelengths of light. Filter 76 is not required to reflect light to additional optical components of the system and is therefore set at an incidence of 90 degrees. This setting allows steeper edges to the transmission band of the filter 76, which is important for the optical channel with the least wavelength separation from the illumination source.

This optical system 4, using well designed filters, allow photodiodes 72 and 92 to detect fluorescent signals many orders of magnitude lower in intensity than that of the illumination source (flashlamp 8). In operation, the fluorescence channels detect essentially no light in the absence of an optical fiber 48. Even placing a reflector at the position of optical fiber 48 results in essentially no detection of false fluorescence.

A schematic diagram of the electronics system 100 that accompanies the optical system 4 (FIG. 6) of the fluorometer is shown in FIG. 7. All functions of the fluorometer are under microprocessor control. There are two detector channels, one for 600 nm and another for 680 nm light. Each detector is composed of a high sensitivity, low noise photodiode connected to suitable amplifiers, analog to digital (A/D) converter then to the microprocessor. Each channel is identical. A description of one such channel follows.

Light contacting the 600 nm photodiode 92 is converted to a weak electrical current, with the current proportional to the intensity of the light. This current is amplified through two separate transimpedence amplifiers 104 and 108 into a positive and a negative voltage. These voltages are conducted into a true differential amplifier 112 where the voltage signals are combined into a higher voltage signal, with the voltage out proportional to the illumination intensity on the photodiode 92. This scheme of differential amplification is used to reduce common mode noise that may be present due to the small signals generated by the photodiode 92, in comparison to electrical noise that may be generated by the high current flashlamp 8 (FIG. 6).

The voltage from amplifier 112 is fed into amplifier 116, where additional voltage amplification occurs. Additionally, auto zero circuit 120 feeds a signal into amplifier 116 that is proportional to the signal present from amplifier 112 when the flashlamp 8 is not firing. This auto zero signal is substacted from that of amplifier 112, so as to yield essentially zero output from amplifier 116 except when light is actually falling on the photodiode 92. This autozero feature automatically corrects for amplifier drift and the like, and ensures the output from amplifier 116 is proportional to the light intensity during the flash. Careful design of the auto zero circuit 120 also helps to eliminate ambient light signals that may be present when the fiber 48 (FIG. 6) is illuminated from an external white light source, such as room or examining lights. Finally, another part of amplifier 116 converts the voltage output to a true current source for feeding into the A/D converter 124.

The A/D converter 124 is a 20 bit charge integrating device. During operation, the integration period is 300 microseconds. That is, the A/D converter 124 measures the total charge from amplifier 116 over a 300 microsecond period. Operation starts with the A/D converter 124 measuring a background period, with no light from the flashlamp 8 (FIG. 6). This is followed by triggering the flashlamp (from the microprocessor 128) and measuring the total signal from the photodiodes 92 and 72. Since the flash is 100 microseconds long, the A/D converter 124 is timed to capture all of the signal in this integration period. The A/D converter 124 then measures another period without the flashlamp 8 (FIG. 6). The first and third periods are averaged and subtracted from the signal during the second period to remove additional background. In this way, additional noise and ambient light effects are removed. The A/D converter 124 is chosen to have 20 bit resolution to accurately handle large changes in detected light from different probes, aging effects in the optics, and so forth, without need for an auto gain circuit. It must be remembered that in this system, the pH is determined by the ratio between fluorescence at 600 nm and at 680 nm, not in their absolute magnitudes. The fluorometer thus disclosed accurately measures this ratio automatically regardless of the instrument, probe, or ambient changes.

The microprocessor 128 measures the signals from both of the A/D converters 124 and 132 simultaneously, and generates a pulse ratio of fluorescence for each flashlamp pulse. Additionally, it can further average or process the signal as required. As previously mentioned, it also controls the A/D converters 124 and 132, flashlamp trigger 136, and auto zero timing 140 functions. The ratio of fluorescence calculated by the microprocessor 128 is converted to pH data, which is transmitted to a pH data output device 144.

EXAMPLE 25

Figure 4:
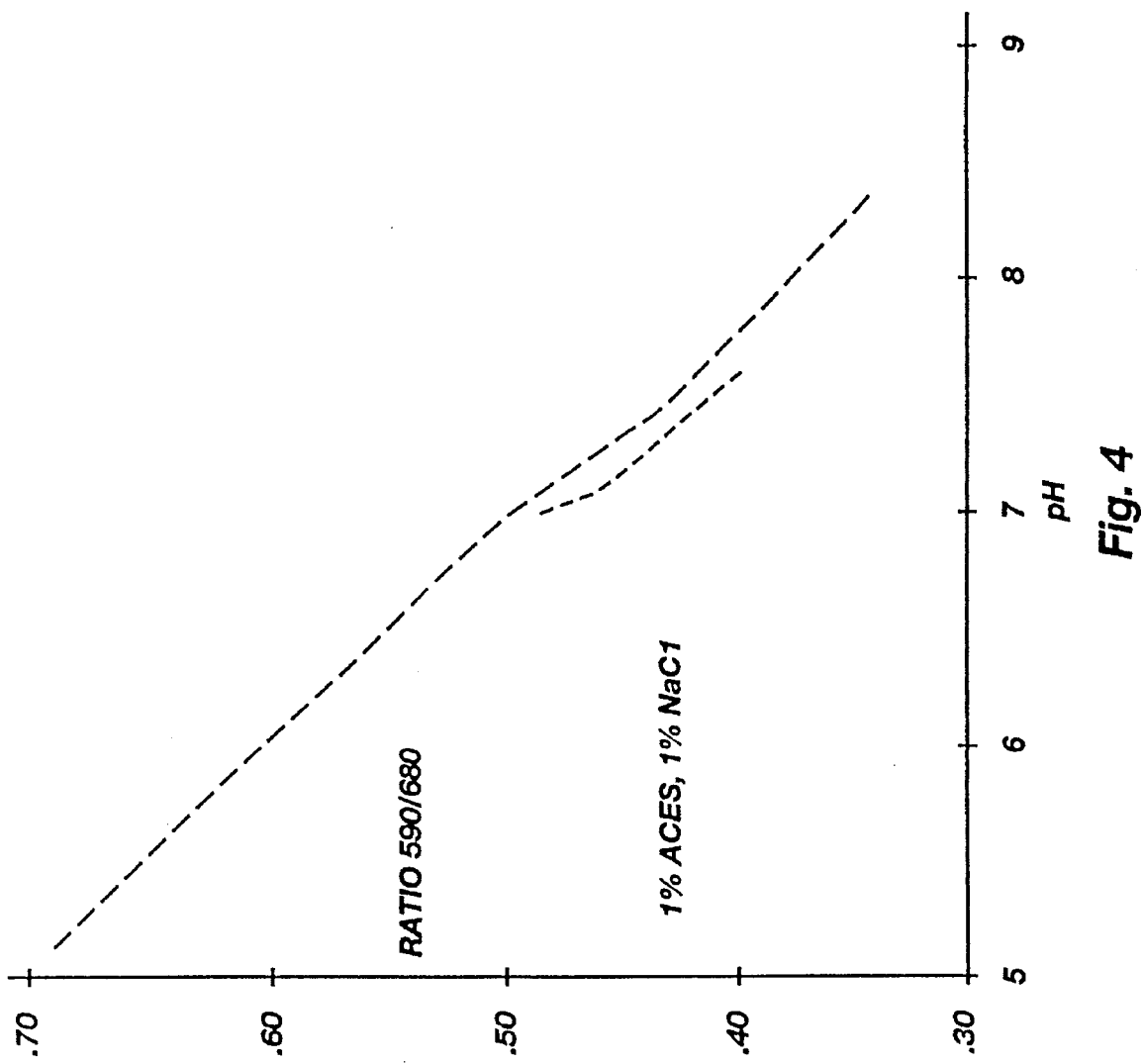
FIG. 4 shows a graphic representation of emission ratio (emission at 590 nm divided by emission at 680 nm) as a function of pH for buffer samples analyzed with a fiber optic pH measurement system according to the present invention.

Buffer solutions (1% ACES, 1% NaCl) were made and adjusted to pH values between approximately 5 and 9 and read at room temperature on a freshly calibrated Orion Model 720 pH meter. Optical pH data from each buffer sample were collected electronically with the computerized data acquisition system. After coming to equilibrium, 100 readings were taken of each sample. The results of this experiment are shown in FIG. 4, wherein the emission ratio (emission at 590 nm divided by the emission at 680 nm) is presented as a function of pH. The precision of each ratio data point was typically better than 0.5%, which yields a pH uncertainty of approximately 0.02 pH unit at ±1 standard deviation.

EXAMPLE 26

Protein-containing buffer samples (1% BSA, 1% ACES, 1% NaCl) were prepared in the pH of range of 6.9 to 7.6.

Figure 5:
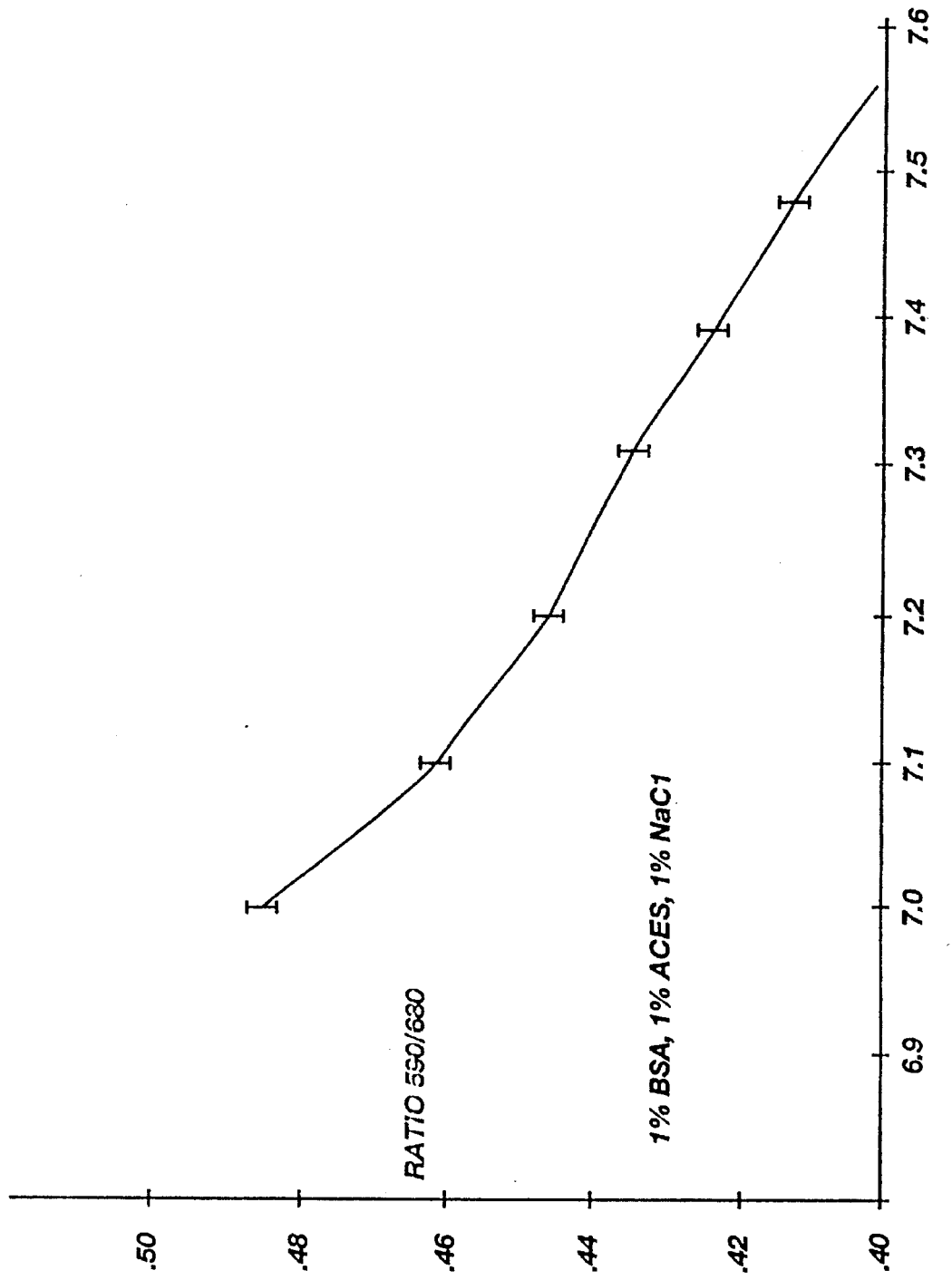
FIG. 5 shows a graphic representation of emission ratio as a function of pH for protein-containing buffer samples with a fiber optic pH measurement system according to the present invention.

These samples were subjected to pH determination according to the procedure of Example 25. The resulting data are summarized in FIG. 5. As in Example 25, the precision of each data point and the slope of the emission ratio/pH curve yielded a pH uncertainty of about 0.02 pH unit.

From the foregoing, it will be appreciated that the compositions of the present invention comprise means for pH determination using a wide range of solid support materials. It is therefore possible to utilize a particular carbazine dye, solid support, and covalent linking means to provide optimal pH measurement.

The present invention may be embodied in other specific forms without departing from its spirit or essential characteristics. The described embodiments are to be considered in all respects only as illustrative and not restrictive. The scope of the invention is, therefore, limited only by the appended claims rather than by the foregoing description. All changes which come within the meaning and range of functional equivalency of the claims are to be embraced within their scope.

I claim:

1. A composition for indicating pH of a solution into which the composition is placed comprising a fluorescent carbazine dye covalently bonded to a solid support, said dye-support composition represented by the formula:

D-B-M wherein M is any solid support containing or derivatized to contain a functional group reactive with hydrazine such that reaction with hydrazine forms a hydrazine-derivatized solid support; D is any fluorescent carbazine dye represented by the formula

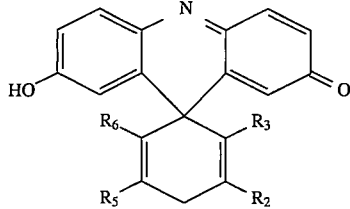

wherein $R_2$, $R_3$, $R_5$, and $R_6$ are each selected from the group consisting of H and alkyl, and wherein said fluorescent carbazine dye is reactive with the hydrazine-derivatized solid support at the 1-carbon of the spiro ring; and B is a covalent linkage formed by reaction between the hydrazine-derivatized solid support and the 1-carbon of the spiro ring, and is selected from the group consisting of —NHNH—, =N—NH—, and =N—N=.

2. The composition of claim 1 wherein D is a single excitation, dual emission carbazine dye.

3. The composition of claim 1 wherein M is a member selected from the group consisting of a periodate-oxidation-susceptible polymer, epoxide-reactive support, inorganic support, polyaldehyde polymer, and poly(methyl ketone) polymer.

4. The composition of claim 3 wherein M is a periodate-oxidation-susceptible polymer.

5. The composition of claim 4 wherein M is a member selected from the group consisting of paper, starch, cellulose, amylose, rayon, cellophane, and mixtures thereof.

6. The composition of claim 5 wherein B is —NHNH—.

7. The composition of claim 3 wherein M is an epoxide-reactive support.

8. The composition of claim 7 wherein the epoxide-reactive polymer contains a surface functional group selected from the group consisting of hydroxyl, amino, carboxylic acid, and anhydride.

9. The composition of claim 3 wherein M is an inorganic support.

10. The composition of claim 9 wherein the inorganic support is a member selected from the group consisting of glass, glass fibers, sand, silica gel, alumina, titania, nickel oxide, aluminum oxide, zirconia, and mixtures thereof.

11. The composition of claim 10 wherein the inorganic support is a member selected from the group consisting of glass, glass fibers, sand, silica gel, alumina, and mixtures thereof.

12. The composition of claim 11 wherein B is —NHNH—.

13. The composition of claim 3 wherein M is a polyaldehyde polymer.

14. The composition of claim 13 wherein the polyaldehyde polymer is a member selected from the group consisting of polyacrolein and polymerized glutaraldehyde.

15. The composition of claim 14 wherein B is —NHNH—.

16. The composition of claim 3 wherein M is a poly(methyl ketone) polymer.

17. The composition of claim 16 wherein B is =N—N=.

18. The composition of claim 3 wherein $R_2$, $R_3$, $R_5$, and $R_6$ are each H.

19. The composition of claim 3 wherein $R_2$ and $R_6$ are each H and $R_3$ and $R_5$ are each methyl.

20. The composition of claim 3 wherein $R_2$, $R_3$, and $R_5$ are each methyl and $R_6$ is H.

21. The composition of claim 3 wherein $R_2$, $R_3$, $R_5$, and $R_6$ are each methyl.

22. The composition of claim 3 wherein $R_2$ and $R_3$ are cyclohexyl and $R_5$ and $R_6$ are each H.

23. The composition of claim 3 wherein $R_2$ and $R_6$ are each H, $R_3$ is isopropyl, and $R_5$ is methyl.

24. A composition of matter for use as a pH indicator comprising a fluorescent carbazine dye covalently bonded to hydrazine or a substituted hydrazine, wherein said composition is a member selected from the group consisting of

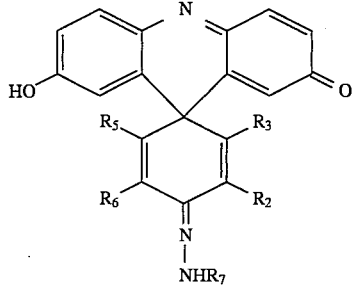

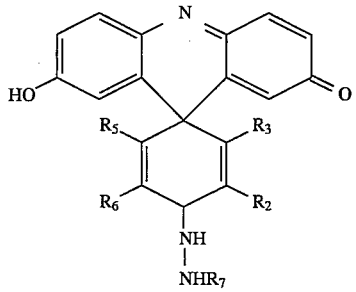

-continued

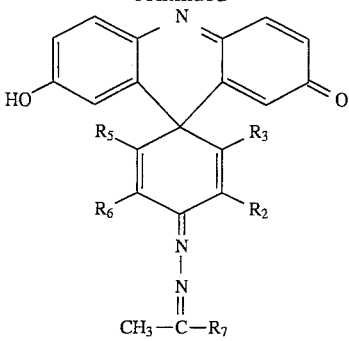

wherein $R_2$, $R_3$, $R_5$, and $R_6$ are each selected from the group consisting of H and alkyl, and $R_7$ is selected from the group consisting of H and alkyl.

25. The composition of claim 24 wherein said carbazine dye is a single excitation, dual emission carbazine dye.

26. The composition of claim 24 wherein wherein $R_2$, $R_3$, $R_5$, and $R_6$ are each H.

27. The composition of claim 24 wherein $R_2$ and $R_6$ are each H and $R_3$ and $R_5$ are each methyl.

28. The composition of claim 24 wherein $R_2$, $R_3$, and $R_5$ are each methyl and $R_6$ is H.

29. The composition of claim 24 wherein $R_2$, $R_3$, $R_5$, and $R_6$ are each methyl.

30. The composition of claim 24 wherein $R_2$ and $R_3$ are cyclohexyl and $R_5$ and $R_6$ are each H.

31. The composition of claim 24 wherein $R_2$ and $R_6$ are each H, $R_3$ is isopropyl, and $R_5$ is methyl.

32. The composition of claim 24 wherein said composition is represented by the formula

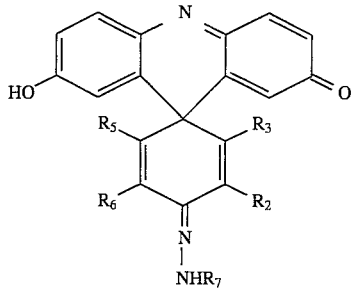

wherein $R_2$, $R_3$, $R_5$, and $R_6$ are each selected from the group consisting of H and alkyl, and $R_7$ is selected from the group consisting of H and alkyl.

33. The composition of claim 24 wherein said composition is represented by the formula

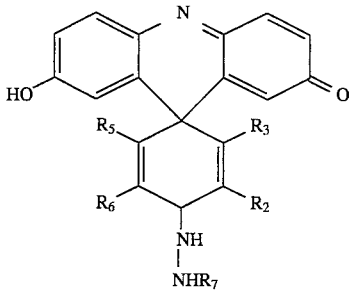

wherein $R_2$, $R_3$, $R_5$, and $R_6$ are each selected from the group consisting of H and alkyl, and $R_7$ is selected from the group consisting of H and alkyl.

34. The composition of claim 24 wherein said composition is represented by the formula

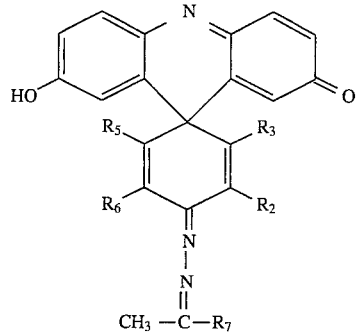

wherein $R_2$, $R_3$, $R_5$, and $R_6$ are each selected from the group consisting of H and alkyl, and $R_7$ is selected from the group consisting of H and alkyl.

35. A fiber optic system for determining pH comprising:

(a) a probe for indicating pH of a solution into which the probed in placed comprising a fluorescent carbazine dye covalently bonded to a solid support, said dye-support composition represented by the formula:

D-B-M wherein M is any solid support containing or derivatized to contain a functional group reactive with hydrazine such that reaction with hydrazine forms a hydrazine-derivatized solid support; D is any fluorescent carbazine dye represented by the formula

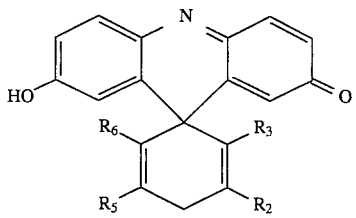

wherein $R_2$, $R_3$, $R_5$, and $R_6$ are each selected from the group consisting of H and alkyl, and wherein said fluorescent carbazine dye is reactive with the hydrazine-derivatized solid support at the 1-carbon of the spiro ring; and B is a covalent linkage formed by reaction between the hydrazine-derivatized solid support and the 1-carbon of the spiro ring, and is selected from the group consisting of —NHNH—, =N—NH—, and =N—N=;

(b) an optical fiber coupled to said probe for receiving excitation light from a fluorometer and conducting said excitation light to said probe and for receiving emitted light from said probe and conducting said emitted light to said fluorometer;

(c) a fluorometer coupled to said optical fiber for generating excitation light at a selected wavelength and delivering said excitation light to said fiber, receiving and measuring intensities of said emitted light at a first selected wavelength and at a substantially different second selected wavelength, and generating an electronic signal containing measurements of said intensities; and (d) means coupled to said fluorometer for receiving said electronic signal, calculating a ratio of said measurements of said intensities, correlating said ratio to a previously determined relationship with pH, and displaying said pH.

36. The system of claim 35 wherein D is a single excitation, dual emission carbazine dye.

37. The system of claim 35 wherein M is is a member selected from the group consisting of a periodate-oxidation-susceptible polymer, epoxide-reactive support, inorganic support, polyaldehyde polymer, and poly(methyl ketone) polymer.

38. The system of claim 37 wherein M is a periodate-oxidation-susceptible polymer.

39. The system of claim 38 wherein M is a member selected from the group consisting of paper, starch, cellulose, amylose, rayon, cellophane, and mixtures thereof.

40. The system of claim 39 wherein B is —NHNH—.

41. The system of claim 37 wherein M is an epoxide-reactive support.

42. The system of claim 41 wherein the epoxide-reactive support contains a surface functional group selected from the group consisting of hydroxyl, amino, carboxylic acid, and anhydride.

43. The system of claim 37 wherein M is an inorganic support.

44. The system of claim 43 wherein the inorganic support is a member selected from the group consisting of glass, glass fibers, sand, silica gel, alumina, titania, nickel oxide, aluminum oxide, zirconia, and mixtures thereof.

45. The system of claim 44 wherein the inorganic support is a member selected from the group consisting of glass, glass fibers, sand, silica gel, alumina and mixtures thereof.

46. The system of claim 45 wherein B is —NENH—.

47. The system of claim 37 wherein M is a polyaldehyde polymer.

48. The system of claim 47 wherein the polyaldehyde polymer is a member selected from the group consisting of polyacrolein and polymerized glutaraldehyde.

49. The system of claim 48 wherein B is —NHNH—.

50. The system of claim 37 wherein M is a poly(methyl ketone) polymer.

51. The system of claim 50 wherein B is =N—N=.

52. The system of claim 37 wherein $R_2$, $R_3$, $R_5$, and $R_6$ are each H.

53. The system of claim 37 wherein $R_2$ and $R_6$ are each H and $R_3$ and $R_5$ are each methyl.

54. The system of claim 37 wherein $R_2$, $R_3$, and $R_5$ are each methyl and $R_6$ is H.

55. The system of claim 37 wherein $R_2$, $R_3$, $R_5$, and $R_6$ are each methyl.

56. The system of claim 37 wherein $R_2$ and $R_3$ are cyclohexyl and $R_5$ and $R_6$ are each H.

57. The system of claim 37 wherein $R_2$ and $R_6$ are each H, $R_3$ is isopropyl, and $R_5$ is methyl.

58. The system of claim 35 wherein said fiber comprises a plastic fiber.

59. The system of claim 35 wherein said selected wavelength of excitation light is in the range of about 480 to about 540 nm.

60. The system of claim 59 wherein said first selected wavelength of emitted light is in the range of about 570 to about 620 nm, and said second selected wavelength of emitted light is in the range of about 650 to about 720 nm.

61. A method of determining pH of a solution comprising the steps of:

(a) providing a composition comprising a fluorescent carbazine dye covalently bonded to a solid support, said dye-support composition represented by the formula:

D-B-M wherein M is any solid support containing or derivatized to contain a functional group reactive with hydrazine such that reaction with hydrazine forms a hydrazine-derivatized solid support; D is any fluorescent carbazine dye represented by the formula

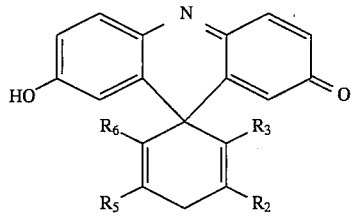

wherein $R_2$, $R_3$, $R_5$, and $R_6$ are each selected from the group consisting of H and alkyl, and wherein said fluorescent carbazine dye is reactive with the hydrazine-derivatized solid support at the 1-carbon of the spiro ring; and B is a covalent linkage formed by reaction between the hydrazine-derivatized solid support and the 1-carbon of the spiro ring, and is selected from the group consisting of —NHNH—, =N—NH—, and =N—N=;

(b) placing said composition in the solution for which pH is to be determined;

(c) contacting said composition in the solution with light of a selected wavelength for exciting emission of fluorescent light by said carbazine dye;

(d) measuring intensities of said fluorescent light at a first selected wavelength and at a substantially different second selected wavelength;

(e) calculating a ratio of said measurements of intensity at said first selected wavelength and said second selected wavelength; and (f) correlating said ratio with a predetermined relationship of ratios to pH.

62. The method of claim 61 wherein D is a single excitation, dual emission carbazine dye.

63. The method of claim 61 wherein M is a member selected from the group consisting of a periodate-oxidation-susceptible polymer, epoxide-reactive support, inorganic support, polyaldehyde polymer, and poly(methyl ketone) polymer.

64. The method of claim 63 wherein M is a periodate-oxidation-susceptible polymer.

65. The method of claim 64 wherein M is a member selected from the group consisting of paper, starch, cellulose, amylose, rayon, cellophane, and mixtures thereof.

66. The method of claim 65 wherein B is —NHNH—.

67. The method of claim 63 wherein M is an epoxide-reactive support.

68. The method of claim 67 wherein the epoxide-reactive support contains a surface functional group selected from the group consisting of hydroxyl, amino, carboxylic acid, and anhydride.

69. The method of claim 63 wherein M is an inorganic support.

70. The method of claim 69 wherein the inorganic support is a member selected from the group consisting of glass, glass fibers, sand, silica gel, alumina, titania, nickel oxide, aluminum oxide, zirconia, and mixtures thereof.

71. The method of claims 70 wherein the inorganic support is a member selected from the group consisting of glass, glass fibers, sand, silica gel, alumina, and mixtures thereof.

72. The method of claim 71 wherein B is —NHNH—.

73. The method of claim 63 wherein M is a polyaldehyde polymer.

74. The method of claim 73 wherein the polyaldehyde polymer is a member selected from the group consisting of polyacrolein and polymerized glutaraldehyde.

75. The method of claim 74 wherein B is —NHNH—.

76. The method of claim 63 wherein M is a poly(methyl ketone) polymer.

77. The method of claim 76 wherein B is =N—N=.

78. The method of claim 63 wherein $R_2$, $R_3$, $R_5$, and $R_6$ are each H.

79. The method of claim 63 wherein $R_2$ and $R_6$ are each H and $R_3$ and $R_5$ are each methyl.

80. The method of claim 63 wherein $R_2$, $R_3$, and $R_5$ are each methyl and $R_6$ is H.

81. The method of claim 63 wherein $R_2$, $R_3$, $R_5$, and $R_6$ are each methyl.

82. The method of claim 63 wherein $R_2$ and $R_3$ are cyclohexyl and $R_5$ and $R_6$ are each H.

83. The method of claim 63 wherein $R_2$ and $R_6$ are each H, $R_3$ is isopropyl, and $R_5$ is methyl.

* * * * *